(12) United States Patent
Ye et al.

(10) Patent No.: US 11,874,212 B2
(45) Date of Patent: Jan. 16, 2024

(54) BLOOD ANALYSIS METHOD, BLOOD ANALYSIS SYSTEM AND STORAGE MEDIUM

(71) Applicant: Shenzhen Mindray Bio-Medical Electronics Co., Ltd., Shenzhen (CN)

(72) Inventors: Bo Ye, Shenzhen (CN); Wenbo Zheng, Shenzhen (CN); Huan Qi, Shenzhen (CN); Zhaoyang Li, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 750 days.

(21) Appl. No.: 17/078,740

(22) Filed: Oct. 23, 2020

(65) Prior Publication Data

US 2021/0041343 A1 Feb. 11, 2021

Related U.S. Application Data

(63) Continuation of application No. PCT/CN2019/084684, filed on Apr. 26, 2019.

(30) Foreign Application Priority Data

Apr. 28, 2018 (WO) ................ PCT/CN2018/085195

(51) Int. Cl.
*G01N 15/14* (2006.01)
*G01N 15/10* (2006.01)
*G01N 33/49* (2006.01)

(52) U.S. Cl.
CPC ..... *G01N 15/1429* (2013.01); *G01N 15/1031* (2013.01); *G01N 33/49* (2013.01)

(58) Field of Classification Search
CPC ............... G01N 15/1031; G01N 15/12; G01N 15/1429; G01N 15/1459;
(Continued)

(56) References Cited

U.S. PATENT DOCUMENTS 5,116,539 A   5/1992   Hamaguchi et al.
5,532,139 A   7/1996   Miller
(Continued)

FOREIGN PATENT DOCUMENTS

CA   2218728 A1   10/1996
CN   101464245 A   6/2009
(Continued)

OTHER PUBLICATIONS

China National Intellectual Property Administration, Chinese Application No. 201980008269.5, Office Action dated Nov. 10, 2022, 6 pages.

*Primary Examiner* — Jennifer Wecker
(74) *Attorney, Agent, or Firm* — Kory D. Christensen

(57) ABSTRACT

A blood analysis method, a blood analysis system, and a storage medium are provided. The blood analysis method includes: providing a blood sample; mixing a first aliquot of the blood sample with a diluent to prepare a first test sample; mixing a second aliquot of the blood sample with a lytic reagent to prepare a second test sample; detecting electrical impedance signals of the first test sample to obtain first volume distribution data; detecting at least two types of optical signals of the second test sample to obtain second volume distribution data; acquiring red blood cell test data of the blood sample; determining, based on the first volume distribution data, the second volume distribution data, and the red blood cell test data, whether the blood sample contains schistocytes; and if the determination result is yes, providing a warning that the blood sample may contain schistocytes.

17 Claims, 14 Drawing Sheets

(58) Field of Classification Search
CPC ... G01N 2015/0084; G01N 2015/1006; G01N 2015/1037; G01N 2015/1402; G01N 2015/1486; G01N 33/48; G01N 33/49
See application file for complete search history.

(56) References Cited

U.S. PATENT DOCUMENTS

| | | |
|---|---|---|
| 6,472,215 B1 | 10/2002 | Huo et al. |
| 2001/0053551 A1 | 12/2001 | Jiang et al. |
| 2007/0054403 A1 | 3/2007 | Zheng et al. |
| 2011/0178716 A1* | 7/2011 | Krockenberger .. G01N 33/4915 702/19 |
| 2016/0282346 A1* | 9/2016 | Suzuki ............... G01N 33/4915 |

FOREIGN PATENT DOCUMENTS

| | | |
|---|---|---|
| CN | 101470109 A | 7/2009 |
| CN | 102713914 A | 10/2012 |
| CN | 103472034 A | 12/2013 |
| CN | 104297135 A | 1/2015 |
| CN | 105074420 A | 11/2015 |
| CN | 107817208 A | 3/2018 |
| EP | 2182345 A1 | 5/2010 |
| JP | 10311785 A | 11/1998 |
| WO | 2009150327 A2 | 12/2009 |

* cited by examiner

BLOOD ANALYSIS METHOD, BLOOD ANALYSIS SYSTEM AND STORAGE MEDIUM

CROSS-REFERENCE

This application is a continuation of International Application No. PCT/CN2019/084684, filed Apr. 26, 2019, which claims priority benefit of International Application No. PCT/CN2018/085195, filed Apr. 28, 2018, the contents of which are incorporated herein by reference.

TECHNICAL FIELD

The present disclosure relates to the field of in vitro detection, and in particular, to a blood analysis method, a blood analysis system and a storage medium thereof.

BACKGROUND ART

Blood analysis is widely used in medical research and detection to acquire related information about blood cells including red blood cells, white blood cells, platelets, etc. Commonly used automated blood analyzers generally analyze blood cells in blood samples based on the electrical impedance principle (also known as Coulter Principle). According to the electrical impedance principle, when particles suspended in an electrolyte pass through a detection aperture with the electrolyte, the equivalent resistance across the detection aperture will change. Under effect of a constant current source cross the detection aperture, the voltage across the detection aperture will change. The changes in the voltage across the detection aperture are collected by a circuit system, and voltage pulse waveforms can thus be generated, wherein amplitudes of the pulse waveforms reflect volume sizes of the particles. The analyzers can provide information about volume distribution of particles in samples according to the acquired pulse waveforms. For blood samples, the blood analyzers can provide a volume distribution histogram of blood cells in a test blood sample based on the electrical impedance principle, and then acquire blood analysis data such as cell classification, cell count and the like by analyzing the volume distribution histogram.

However, detection signals based on the electrical impedance principle can only reflect information about volume of particles passing through the detection aperture, and cannot be used to differentiate among different particles with a same or similar volume. For example, blood cell analysis methods based on the electrical impedance method cannot be used to differentiate among large platelets, red blood cell fragments (schistocytes, RBC fragments) and microcytes with a similar volume, and the methods may mistakenly count a red blood cell with relatively small volume (such as a red blood cell fragment and a microcyte) as a platelet. U.S. Pat. No. 6,670,191 discloses a method for analyzing schistocytes by detecting intensities of scattered light and fluorescent light of a fluorescently stained blood sample. This method requires a special reagent and a detection channel to detect schistocytes, thereby increasing costs of apparatus and reagents for blood cell analysis.

SUMMARY

An aspect of embodiments of the present disclosure includes a blood analysis method, including the following steps: providing a blood sample; mixing a first aliquot of the blood sample with a diluent agent to prepare a first test sample; mixing a second aliquot of the blood sample with a lytic reagent to prepare a second test sample, wherein red blood cells in the second test sample are lysed by the lytic reagent; detecting electrical impedance signals of the first test sample; detecting at least two types of optical signals of the second test sample; acquiring first volume distribution data of the first test sample based on the electrical impedance signals; generating a scattergram of the second test sample based on the at least two types of optical signals; identifying a non-white blood cell region in the scattergram based on the at least two types of optical signals; and acquiring second volume distribution data of the second test sample based on the non-white blood cell region; acquiring red blood cell detection data of the blood sample; determining whether the blood sample may contain schistocytes based on the first volume distribution data, the second volume distribution data and the red blood cell detection data; and providing an alarm for indicating that the blood sample may contain schistocytes if the determination result is yes.

Further, in the blood analysis method provided by embodiments of the present disclosure, the lytic reagent includes a hemolytic agent for lysing red blood cells and a fluorescence dye for staining blood cells, and the at least two types of optical signals include forward scattered light signals and fluorescent signals.

Further, in the blood analysis method provided by embodiments of the present disclosure, the lytic reagent includes a hemolytic agent for lysing red blood cells, and the at least two types of optical signals include first scattered light signals and second scattered light signals, wherein the first scattered light signals are forward scattered light signals, and the second scattered light signals are at least one type of medium-angle scattered light signals and side scattered light signals.

Further, in the blood analysis method provided by embodiments of the present disclosure, acquiring second volume distribution data of the second test sample based on the non-white blood cell region includes: acquiring the second volume distribution data of the second test sample based on at least forward scattered light signals of a particle population characterized in the non-white blood cell region.

Further, the blood analysis method provided by embodiments of the present disclosure further includes: acquiring a second particle number of particles within a preset volume range of the second volume distribution data.

Further, in the blood analysis method provided by embodiments of the present disclosure, acquiring second volume distribution data of the second test sample based on the non-white blood cell region includes: identifying a large platelet region in the non-white blood cell region; and acquiring a second particle number of the second test sample based on at least forward scattered light signals of a particle population characterized in the large platelet region.

Further, in the blood analysis method provided by embodiments of the present disclosure, acquiring second volume distribution data of the second test sample based on the non-white blood cell region includes: identifying a large platelet region in the non-white blood cell region; and acquiring a second particle number of the second test sample based on a number of particles in the large platelet region.

Further, in the blood analysis method provided by embodiments of the present disclosure, determining whether the blood sample may contain schistocytes includes: acquiring a first particle number of particles within a preset volume range of the first volume distribution data; acquiring a difference degree by comparing the first particle number and the second particle number; and determining whether the difference degree meets a preset condition; determining whether the blood sample is a microcyte sample based on the red blood cell detection data; and determining that the blood sample may contain schistocytes when the difference degree meets the preset condition and the blood sample is not a microcyte sample.

Further, in the blood analysis method provided by embodiments of the present disclosure, determining whether the blood sample may contain schistocytes includes: determining whether the first volume distribution data of the first test sample is abnormal; acquiring a second particle number based on the second volume distribution data of the second test sample, and determining whether the second particle number exceeds a threshold; determining whether the blood sample is a microcyte sample based on the red blood cell detection data; and determining that the blood sample may contain schistocytes when the first distribution data are abnormal, the second particle number does not exceed the threshold and the blood sample is not a microcyte sample.

Further, in the blood analysis method provided by embodiments of the present disclosure, acquiring red blood cell detection data of the blood sample includes: acquiring a mean corpuscular volume (MCV) of the blood sample based on the electrical impedance signals.

Further, in the blood analysis method provided by embodiments of the present disclosure, determining whether the blood sample is a microcyte sample based on the red blood cell detection data includes: determining whether the MCV is greater than a preset MCV threshold; when the MCV is greater than the preset MCV threshold, the blood sample is not a microcyte sample.

Further, in the blood analysis method provided by embodiments of the present disclosure, acquiring red blood cell detection data of the blood sample includes: acquiring volume distribution data of red blood cells of the blood sample based on the electrical impedance signals; and acquiring a volume at a preset volume percentage quantile of red blood cells based on the volume distribution data of red blood cells.

Further, in the blood analysis method provided by embodiments of the present disclosure, determining whether the blood sample is a microcyte sample based on the red blood cell detection data includes: determining whether the volume at the preset volume percentage quantile of red blood cells is greater than a preset threshold; when the volume at the preset volume percentage quantile of red blood cells is greater than the preset threshold, the blood sample is not a microcyte sample.

Further, in the blood analysis method provided by embodiments of the present disclosure, the two types of optical signals include scattered light signals and fluorescent signals, and the method further includes: classifying white blood cells in the sample into white blood cell subpopulations, or counting white blood cells or identifying nucleated red blood cells or immature cells or basophils based on the scattered light signals and the fluorescent signals of the second test sample.

Further, the blood analysis method provided by embodiments of the present disclosure includes: classifying white blood cells in the sample into white blood cell subpopulations or identifying basophils based on scattered light signals of the second test sample.

Another aspect of embodiments of the present disclosure further provides a non-volatile computer-readable storage medium with a computer program stored thereon, wherein the computer program, when executed by a processor, implements steps of any analysis method aforementioned.

Another aspect of embodiments of the present disclosure further provides a blood analysis system, including: a sample treatment device including at least one mixing chamber, which is configured to mix a first aliquot of a blood sample with a diluent agent to prepare a first test sample, and mix a second aliquot of the blood sample with a lytic reagent to prepare a second test sample; a sample detection device including an electrical impedance detection unit and an optical detection unit, wherein the electrical impedance detection unit includes an aperture and an electrical impedance detector, and the electrical impedance detector is configured to detect electrical impedance signals of the first test sample passing through the aperture; the optical detection unit includes an optical flow chamber, a light source and an optical detector, wherein the optical flow chamber is in fluid communication with the mixing chamber, the light source is configured to direct a light beam to the optical flow chamber, and the optical detector is configured to detect at least two types of optical signals of the second test sample passing through the optical flow chamber; and a data analysis module including a signal acquisition module, a classification and counting module and an alarm module; wherein the signal acquisition module is configured acquire the electrical impedance signals of the first test sample, and the at least two types of optical signals of the second test sample; the classification and counting module is configured to acquire first volume distribution data of the first test sample based on the electrical impedance signals, generate a scattergram of the second test sample based on the at least two types of optical signals, differentiate a white blood cell region and a non-white blood cell region in the scattergram based on the at least two types of optical signals, and acquire second volume distribution data of the second test sample based on the non-white blood cell region; and the alarm module is configured to acquire red blood cell detection data of the blood sample, determine whether the blood sample may contain schistocytes based on the first volume distribution data, the second volume distribution data and the red blood cell detection data, and provide an alarm for indicating that the blood sample may contain schistocytes if the determination result is yes.

Further, in the blood analysis system provided by embodiments of the present disclosure, the lytic reagent in the sample treatment device includes a hemolytic agent for lysing red blood cells and a fluorescence dye for staining blood cells, and the at least two types of optical signals in the sample detection device include forward scattered light signals and fluorescent signals, or include forward scattered light signals and side scattered light signals.

Further, in the blood analysis system provided by embodiments of the present disclosure, the lytic reagent in the sample treatment device includes a hemolytic agent for lysing red blood cells, and the at least two types of optical signals in the sample detection device include first scattered light signals and second scattered light signals, wherein the first scattered light signals are forward scattered light signals, and the second scattered light signals are at least one type of medium-angle scattered light signals and side scattered light signals.

Further, in the blood analysis system provided by embodiments of the present disclosure, the classification and counting module is configured to acquire the second volume distribution data of the second test sample based on the forward scattered light signals of a particle population characterized in the non-white blood cell region.

Further, in the blood analysis system provided by embodiments of the present disclosure, the classification and counting module is configured to acquire a second particle number of particles within a preset volume range of the second volume distribution data.

Further, in the blood analysis system provided by embodiments of the present disclosure, the classification and counting module is configured to identify a large platelet region in the non-white blood cell region, and acquire a second particle number of the second test sample based on at least forward scattered light signals of a particle population characterized in the large platelet region.

Further, in the blood analysis system provided by embodiments of the present disclosure, the classification and counting module is configured to identify a large platelet region in the non-white blood cell region, and acquire a second particle number of the second test sample based on a number of particles appearing in the large platelet region.

Further, in the blood analysis system provided by embodiments of the present disclosure, the alarm module is configured to acquire a first particle number of particles within the preset volume range of the first volume distribution data; acquire a difference degree by comparing the first particle number and the second particle number; and determine whether the difference degree meets a preset condition; the alarm module is configured to determine whether the blood sample is a microcyte sample based on the red blood cell detection data; and determine that the blood sample may contain schistocytes when the difference degree meets the preset condition and the blood sample is not a microcyte sample.

Further, in the blood analysis system provided by embodiments of the present disclosure, the classification and counting module is configured to acquire a second particle number based on the second volume distribution data of the second test sample; the alarm module is configured to acquire the first volume distribution data of the first test sample and determine whether the first volume distribution data is abnormal; and acquire the second particle number and determine whether it exceeds a threshold; the alarm module is configured to determine whether the blood sample is a microcyte sample based on the red blood cell detection data; and determine that the blood sample may contain schistocytes when the first distribution data is abnormal, the second particle number does not exceed the threshold and the blood sample is not a microcyte sample.

Further, in the blood analysis system provided by embodiments of the present disclosure, the red blood cell detection data includes a mean corpuscular volume (MCV).

Further, in the blood analysis system provided by embodiments of the present disclosure, the alarm module is configured to determine whether the MCV is greater than a preset MCV threshold; when the MCV is greater than the preset MCV threshold, the blood sample is not a microcyte sample.

Further, in the blood analysis system provided by embodiments of the present disclosure, the red blood cell detection data includes a volume at a preset volume percentage quantile of red blood cells.

Further, in the blood analysis system provided by embodiments of the present disclosure, the alarm module is configured to determine whether the volume at the preset volume percentage quantile of red blood cells is greater than a preset threshold; when the volume at the preset volume percentage quantile of red blood cells is greater than the preset threshold, the blood sample is not a microcyte sample.

Further, in the blood analysis system provided by embodiments of the present disclosure, the classification and counting module is configured to classify white blood cells in the sample into white blood cell subpopulations, or count white blood cells or identify nucleated red blood cells or immature cells or basophils based on scattered light signals and fluorescent signals of the second test sample.

Further, in the blood analysis system provided by embodiments of the present disclosure, the classification and counting module is configured to classify white blood cells in the sample into white blood cell subpopulations or identify basophils based on scattered light signals of the second test sample.

With respect to the prior art, the method, system and storage medium provided by the present disclosure can be realized with relatively low costs, and provide users with more abundant detection information, and remind the users to perform a reexamination or recheck on blood samples that may contain schistocytes.

LIST OF REFERENCE NUMERALS

| | |
|---|---|
| Sample collection unit | 10 |
| Sample treatment device | 30 |
| Mixing chamber | 320, 320a, 320b |
| Sample detection device | 50 |
| Electrical impedance detection unit | 51 |
| Aperture | 512 |
| Electrical impedance detector | 514 |
| Optical detection unit | 53 |
| Optical flow chamber | 532 |
| Light source | 534 |
| Optical detector | 536 |
| Bus | 60 |
| Data analysis module | 70 |
| Storage system | 710 |
| Processor | 730 |
| Signal acquisition module | 750 |
| Classification and counting module | 770 |
| Alarm module | 790 |
| User interface | 90 |
| First housing | 100 |
| Second housing | 200 |

The present disclosure will be further illustrated by the following detailed embodiments of the disclosure in combination with the drawings.

DETAILED DESCRIPTION OF EMBODIMENTS

The technical solution of the present disclosure will be described below with reference to the figures. It should be noted that when one unit is described as being "connected" to another unit, it may be directly connected to another unit or an intermediate unit may exist at the same time. When one unit is described as being "arranged" on another unit, it may be directly arranged on another unit or an intermediate unit may exist at the same time. Unless otherwise defined, all technical and scientific terms used herein have the same meaning as commonly understood by those skilled in the art to which this disclosure belongs. Names of elements or apparatuses used in the specification of the present disclosure are only intended to illustrate the specific embodiments instead of limiting the present disclosure.

A first aspect of the present disclosure relates to a method, system and storage medium for providing an alarm for indicating that a blood sample may contain schistocytes by using electrical impedance signals, scattered light signals and fluorescent signals of the blood sample.

Figure 1:
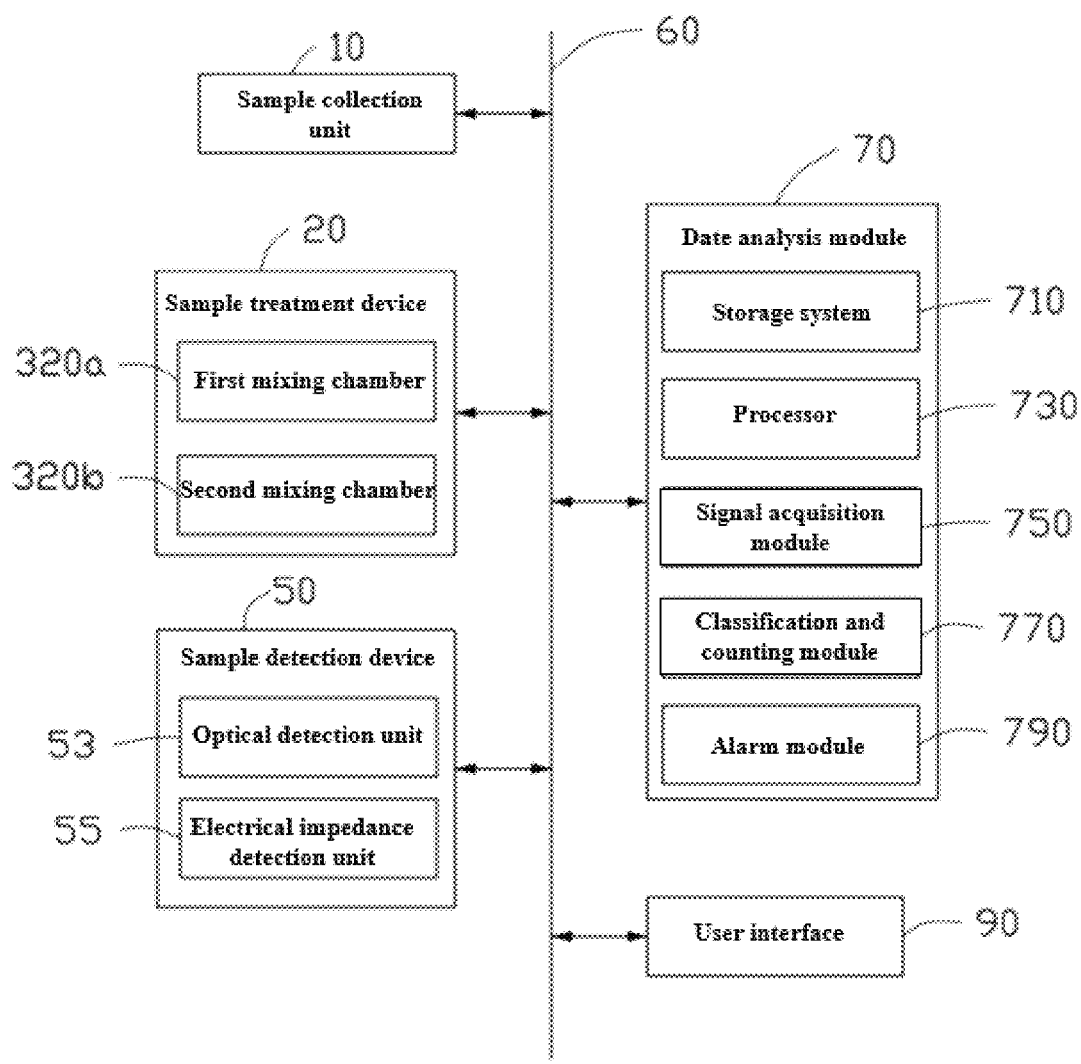
FIG. 1 is a schematic diagram of function modules of a blood analysis system provided by the present disclosure.

FIG. 1 is a schematic diagram of a blood analysis system. The blood analysis system includes a sample collection unit 10, a sample treatment device 30, a sample detection device 50, a data analysis module 70 and a user interface 90. The blood analysis system is provided with a liquid flow system (not shown in the figure), which is configured to make the sample collection unit 10, the sample treatment device 30 and the sample detection device 50 in fluid communication for fluid transfer.

The sample collection unit 10 is configured to supply a blood sample to the sample treatment device 30. The sample treatment device 30 is configured to treat the blood sample for preparing a test sample, and supply the test sample to the sample detection device 50. The sample treatment device 30 may include one or more mixing chambers for preparing the test blood sample into one or more test samples. The sample detection device 50 is configured to detect characteristics of particles in each test sample, and to acquire corresponding detection signals. The data analysis module 70 may be, directly or indirectly, connected electrically with the sample collection unit 10, the sample treatment device 30, the sample detection device 50 and the user interface 90 via a bus 60 to transmit and exchange data or signals.

In a first exemplary implementation of the present disclosure, the sample treatment device 30 includes at least one mixing chamber, which is configured to mix a first aliquot of the test blood sample with a diluent agent to obtain a first test sample, and mix a second aliquot of the test blood sample with a lytic reagent to obtain a second test sample. Alternatively, the sample treatment device 30 may further include a sample dispenser, which is configured to dispense the test blood sample into several aliquots. Each aliquot of blood sample is transferred to the same mixing chamber or different mixing chambers and then treated for subsequent detection. Alternatively, the sample treatment device 30 includes a first mixing chamber 320a and a second mixing chamber 320b for respectively preparing the first test sample and the second test sample. Alternatively, the sample treatment device 30 may include only one mixing chamber for preparing the first test sample and the second test sample one after another.

Specifically, the diluent agent for preparing the first test sample is generally used for diluting blood samples to detect red blood cells and platelets by automated blood analyzers. The diluent agent generally includes one or more salts, such as an alkali metal salt, and is adjusted to be isotonic to maintain volumes of red blood cells. In the implementation of the present disclosure, commercially available diluent agents may be used to dilute the first aliquot of the blood sample to form the first test sample. The commercially available diluent agents include but not limited to M-68DS diluent agent, M-53D diluent agent, etc. which are produced by Shenzhen Mindray Bio-Medical Electronics Co., Ltd. (Shenzhen, China). Temperature and/or stirring conditions for preparing the first test sample may be the same as or similar to sample preparation conditions used by existing automated blood analyzers for detecting red blood cells and platelets.

Specifically, in the first aspect of the present disclosure, the lytic reagent includes a hemolytic agent and a fluorescence dye. The hemolytic agent may be any one of existing hemolytic agents for classifying white blood cells by automated blood analyzers, wherein the hemolytic agent may be any one of a cationic surfactant, a nonionic surfactant, an anionic surfactant and an amphiphilic surfactant or any combination thereof. The fluorescence dye is used for staining blood cells. In some embodiments of the implementation, the fluorescence dye may be a nucleic acid dye, thereby classifying nucleated blood cells, such as white blood cells, and other types of cells by measuring the differences in scattered light signals and fluorescent signals. In an embodiment of the implementation, the lytic reagent may be prepared by using the lytic reagent formula disclosed in U.S. Pat. No. 8,367,358, the entire disclosure of which is incorporated herein by reference. The lytic reagent disclosed in U.S. Pat. No. 8,367,358 includes a cationic cyanine compound (a fluorescence dye), a cationic surfactant, a nonionic surfactant and an anionic compound. The lytic reagent may be used to lyse red blood cells and classify white blood cells into their subpopulations by detecting differences in scattered light intensities and fluorescence intensities. Those skilled in the art may understand that the fluorescence dye may be contained in a separate staining solution, and such a staining solution can be used together with the hemolytic agent without a fluorescence dye. The staining solution may be added to the blood sample in the mixing chamber 320 before, after or upon the hemolytic agent is added for preparing the second test sample. Temperature and/or stirring conditions for preparing the second test sample may be the same as or similar to sample preparation conditions used by existing automated blood analyzers for classifying white blood cells. In another embodiment of the implementation, the fluorescence dye in the lytic reagent may be the fluorescence dye described in U.S. Pat. No. 8,273,329, the entire disclosure of which is incorporated herein by reference. The lytic reagent containing such a fluorescence dye may be adopted to lyse red blood cells, identify and count nucleated red blood cells, white blood cells and the like, and further identify basophils in white blood cells by detecting differences in fluorescence intensities and forward scattered light intensities.

Figure 2:
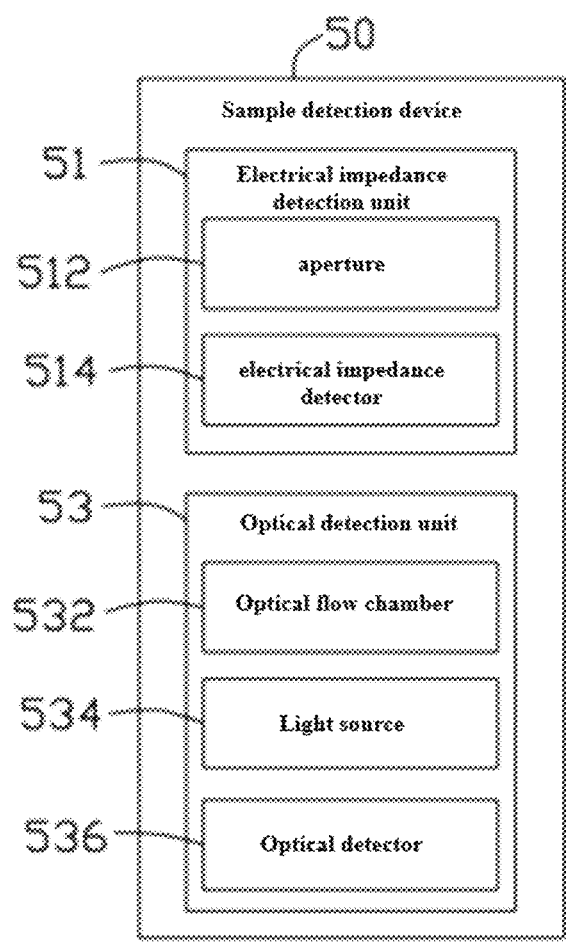
FIG. 2 is a schematic diagram of function modules of a sample detection device of the blood analysis system shown in FIG. 1.

In the first exemplary implementation, the sample detection device 50 of the blood analysis system includes an electrical impedance detection unit 51 and an optical detection unit 53. FIG. 2 is a schematic diagram of function modules of the sample detection device 50.

The electrical impedance detection unit 51 is configured to detect electrical impedance signals of the first test sample. The electrical impedance detection unit 51 includes an aperture 512 and an electrical impedance detector 514. The electrical impedance detector 514 is configured to detect electrical impedance signals of the first test sample when passing through the aperture, such as direct current (DC) impedance signals. It can be understood that, when a particle (or a blood cell) suspended in a conductive solution passes through the aperture, an electrical impedance signal can be detected due to impedance change. The shape, amplitude and width of the pulse generated by the electrical impedance signal are directly related to the size or volume of the particle, and can be converted into the volume of the subject particle. When two or more types of particles with different sizes are detected, a frequency histogram acquired by an electrical impedance detection can reflect a size distribution of these particles. In the prior art, U.S. Pat. Nos. 2,656,508 and No. 3,810,011 describe methods for automatically detecting blood cells by a blood analyzer provided with an electrical impedance unit, the entire disclosure of which is incorporated herein by reference.

The optical detection unit 53 includes a sheath flow system, an optical flow chamber 532, a light source 534, an optical detector 536 and a corresponding detection circuit. The optical flow chamber 532 is operatively in fluid communication with the mixing chamber 320, so that the first test sample is transferred by the sheath flow system from the mixing chamber 320 to the optical flow chamber 532. The light source 534 is configured to direct a light beam to the optical flow chamber 532. The optical detector 536 is configured to detect at least two types of optical signals of the first test sample. In the first exemplary implementation of the present disclosure, the at least two types of optical signals include forward scattered light signals and fluorescent signals. In an embodiment, the optical detector 536 of the optical detection unit 53 is set to be suitable for detecting the forward scattered light signals and the fluorescent signals of the first test sample passing through the optical flow chamber 532. In another embodiment, the at least two types of optical signals further include side scattered light signals, and the optical detector 536 is set to be suitable for detecting the forward scattered light signals, the side scattered light signals and the fluorescent signals of the first test sample passing through the optical flow chamber 532.

Herein, the optical flow chamber refers to a focused-flow flow chamber suitable for detecting scattered light signals and fluorescent signals, for example, the optical flow chambers used in existing flow cytometers and blood analyzers. When a particle, such as a blood cell, passes through an orifice of the optical flow chamber, the incident light beam emitted from the light source and directed to the orifice is scattered by the particle in all directions. By arranging an optical detector at one or more angles with regard to the incident light beam, the light scattered by the particle can be detected to acquire scattered light signals. Since different blood cell populations have different light scattering properties, the scattered light signals can be used to differentiate different cell populations. Specifically, the scattered light signals detected near the incident beam are generally referred to as forward scattered light signals or small-angle scattered light signals. In some embodiments, the forward scattered light signals may be detected at an angle range from about 1° to about 10° with respect to the incident beam. In some other embodiments, the forward scattered light signals may be detected at an angle range from about 2° to about 6° with respect to the incident beam. Scattered light signals detected at an angle of about 90° with respect to the incident beam are generally referred to as side scattered light signals. In some embodiments, the side scattered light signals may be detected at an angle range from about 65° to about 115° with respect to the incident beam. Generally, fluorescent signals emitted from blood cells stained by a fluorescence dye may also be detected at an angle of about 90° with respect to the incident beam.

The data analysis module 70 includes a storage system 710 and a processor 730. The storage system 710 may store basic programs and data structures for implementing various functions of the methods disclosed herein. The storage system 710 may include one or more memories and one or more non-transitory computer-readable storage media. The non-transitory computer-readable storage media may include a Hard Disk Drive (HDD), a floppy disk, an optical disk, a Secure Digital Memory Card (SD Card), a flash memory card or the like. The memory may include a primary Random Access Memory (RAM) for storing program instructions and data or a Dynamic RAM (DRAM) and a Read Only Memory (ROM) for storing fixed instructions. The non-transitory computer-readable storage medium stores computer programs for implementing the methods disclosed by the present disclosure. The processor 730 includes, but is not limited to, a Central Processing Unit (CPU), a Micro Controller Unit (MCU) and other devices for interpreting computer instructions and processing data in computer software. The processor 730 is configured to execute various computer programs in the non-transitory computer-readable storage medium, thereby enabling the blood analysis system to execute the corresponding detection process, analyze and process the at least two types of optical signals detected by the sample detection device 50 in a real-time manner. In exemplary embodiments, the at least two types of optical signals may be processed by a Field-Programmable Gate Array (FPGA), a Digital Signal Processor (DSP) or CPU, and then automatically analyzed by the computer programs to acquire related data of platelets and/or platelet subpopulations.

As shown in FIG. 1, in the first exemplary implementation, the data analysis module 70 further includes a signal acquisition module 750, a classification and counting module 770 and an alarm module 790. The signal acquisition module 750 is operatively connected with the sample detection device 50. The signal acquisition module 750 may respectively acquire the electrical impedance signals of the first test sample and the forward scattered light signals and the fluorescent signals of the second test sample.

The classification and counting module 770 is connected to the signal acquisition module 750. The classification and counting module 770 acquires first volume distribution data of the blood sample based on the electrical impedance signals. The classification and counting module 770 generates a scattergram of the second test sample based on the at least two types of optical signals, differentiates between a white blood cell region and a non-white blood cell region in the scattergram, and then acquires second volume distribution data of the blood sample based on the non-white blood cell region in the scattergram. Scattergram or histogram herein may be presented not only in a graphical form, but also in a data form, for example, in a numeric form of a table or a list with the same or similar resolution as the scattergram or histogram, or may be presented in any other appropriate manner known in the art.

The alarm module 790 is connected to the classification and counting module 770. The alarm module 790 first acquires red blood cell detection data of the blood sample, and then determines whether the blood sample to be test may contain schistocytes based on the first volume distribution data, the second volume distribution data and the red blood cell detection data, and provides an alarm for indicating that the blood sample may contain schistocytes if the determination result is yes. The specific steps executed by the classification and counting module 770 and the alarm module 790 will be described in detail later.

The user interface 90 is a medium for interaction and information exchange between the blood analysis system and users. The user interface 90 may display blood analysis data acquired by the classification and counting module 770 and/or a signal for alarming that the blood sample may contain schistocytes acquired by the alarm module 790 to the users of the blood analysis system. In an embodiment, the user interface 90 may be a touch screen, which can identify touch control operations from users and display detection results. In another embodiment, the user interface 90 may include an input device and an output device. The input device may be a data input medium that is electrically connected to the data analysis module 70, such as a keyboard, a mouse and a microphone, etc. The output device may be a display screen, a printer, a speaker, an indicator light, etc. It can be understood that, when the alarm module 790 provides an alarm for indicating that the blood sample may contain schistocytes, the user interface may prompt users that the platelet detection of the blood sample is abnormal by differentially marking the blood sample with colors, fonts or labels in a detection report or a displayed detection image, or by flashing, sound or other manners.

A blood analysis method for alarming that a blood sample contains schistocytes provided by a second exemplary implementation of the present disclosure will be further described below in detail with reference to the function modules of the blood analysis system described in the first exemplary implementation. It can be understood that the blood analysis method may be used in automated blood analyzers, or may also be used in blood analysis systems provided with a flow cytometer and an electrical impedance detection device. The blood analysis method may be executed by a processor in the form of computer programs. The computer programs may be provided in the automated blood analyzers, or may be independently provided in a computer that can directly or indirectly acquire blood cell detection signal data.

Figure 3:
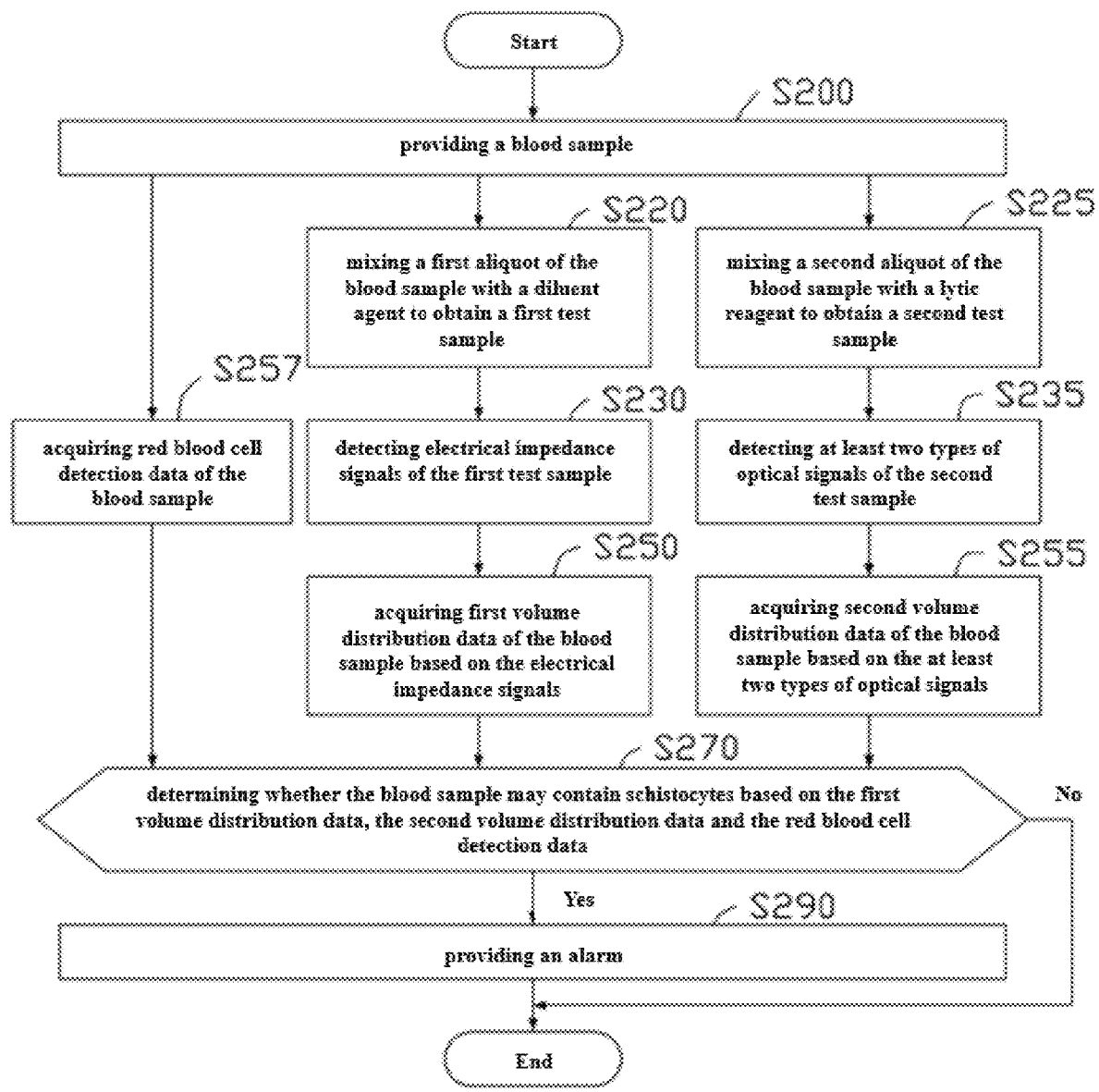
FIG. 3 is a flowchart of a blood analysis method provided by the present disclosure.

Please refer to the flowchart shown in FIG. 3. In the second exemplary implementation, the blood analysis method includes the following steps:

Step S200: providing a blood sample.

Step S220: mixing a first aliquot of the blood sample with a diluent agent to obtain a first test sample.

Step S225: mixing a second aliquot of the blood sample with a lytic reagent to obtain a second test sample. In the second exemplary implementation, the lytic reagent includes a hemolytic reagent for lysing red blood cells and a fluorescence dye for staining blood cells.

Step S230: detecting electrical impedance signals of the first test sample.

Step S235: detecting at least two types of optical signals of the second test sample. In the second exemplary implementation, the at least two types of optical signals include forward scattered light signals and fluorescent signals.

Step S250: acquiring first volume distribution data of the blood sample based on the electrical impedance signals acquired at step S230.

Step S255: acquiring second volume distribution data of the blood sample based on at least the forward scattered light signals acquired at step S235.

Step S257: acquiring red blood cell detection data of the blood sample.

Step S270: determining whether the blood sample may contain schistocytes based on the first volume distribution data, the second volume distribution data and the red blood cell detection data.

If the determination result is yes, step S290 is executed to give an alarm for indicating that the blood sample may contain schistocytes. If the determination result is no, the process ends.

In a specific implementation, when the processor executes step S200, the sample collection unit 10 provides the blood sample for the blood analysis system or the blood analyzer. When the processor executes steps S220 and S225, the sample treatment device 30 respectively prepares the first test sample and the second test sample. Reagents and preparation conditions for preparing the first test sample and the second test sample are described in detail above, which will not be repeated herein. When the processor executes step S230, the electrical impedance detection unit 51 of the sample detection device 50 detects the electrical impedance signals of the first test sample; when the processor executes step S235, the optical detection unit 53 of the sample detection device 50 detects the at least two types of optical signals of the second test sample. When the processor executes steps S250 and S255, the data analysis module 70 respectively acquires the first and second volume distribution data. The processor further executes steps S257, S270 and S290, the alarm module 790 of the data analysis module 70 determines whether the blood sample may contain schistocytes based on the first and second volume distribution data and the red blood cell detection data. It can be understood that, in the flow of the method of the present disclosure, steps S220, S230 and S250 for acquiring the first volume distribution data and steps S225, S235 and S255 for acquiring the second volume distribution data may be executed in parallel or in sequence; step S257 for acquiring the red blood cell detection data may occur at any time between steps S250 and S270, and may occur at any time between step S200 and S270, that is, step S257 may be executed in parallel with steps S220-S250.

At step S250, those skilled in the art should understand that, volume distribution information of blood cells in the first test sample may be acquired based on the electrical impedance signals acquired at step S230, and mainly includes volume distribution information of platelets and red blood cells. An electrical impedance volume histogram may be generated based on the volume distribution information acquired by the electrical impedance method. Generally, in the electrical impedance volume histogram, volumes of blood cells are measured in femtoliter (fL). Platelets can be differentiated from red blood cells in the volume histogram by a preset volume boundary value, and then a volume histogram of platelets, a volume histogram of red blood cells and characteristic parameters of platelets and red blood cells in the blood sample can be respectively acquired. The characteristic parameters include but not limited to platelet count (PLT), Mean Platelet Volume (MPV), Platelet Distribution Width (PDW), red blood cell count (RBC), Mean Corpuscular Volume (MCV) and Red Blood Cell Distribution Width (RDW). It should be noted that "first volume distribution data" herein includes volume distribution information of blood cells and/or characteristic parameters reflecting volume distribution of blood cells in the first test sample. The volume distribution information of blood cells may be presented in a numeric form, or in a graphical form, such as electrical impedance volume histogram. It should be understood that the histogram herein is not limited to a graphic form, but may be presented in a data form.

Figure 4A:
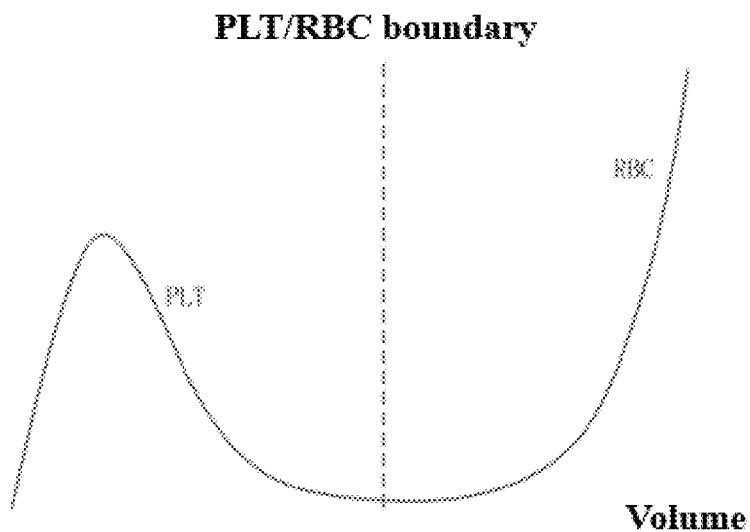
FIG. 4A is an electrical impedance volume histogram of a normal blood sample.
Figure 4B:
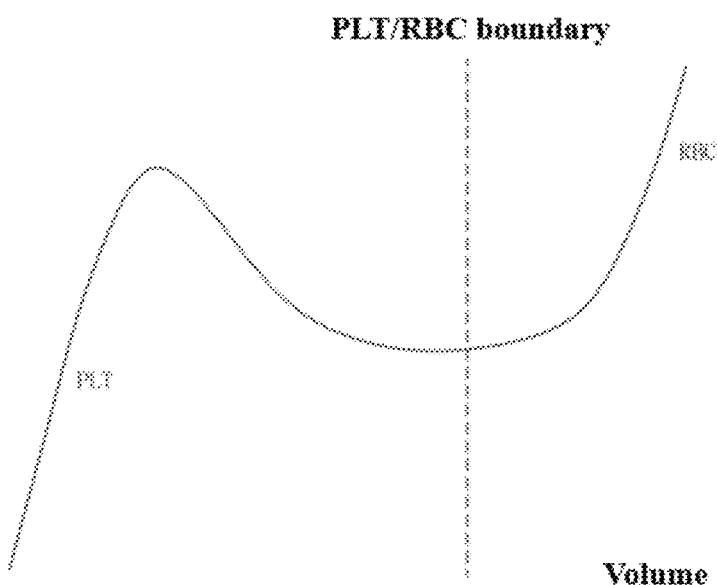
FIG. 4B is an electrical impedance volume histogram of a blood sample containing large platelets, schistocytes or microcytes.

FIG. 4A and FIG. 4B respectively show volume histograms of a normal blood sample and an abnormal blood sample acquired by the electrical impedance detection method. The abnormal blood sample refers to a blood sample containing at least one type of large platelets, schistocytes and microcytes. As shown in FIG. 4A, in the volume histogram of the normal blood sample, the detection peak of platelets can be clearly differentiated from that of red blood cells, and particles corresponding to a volume boundary value for differentiating between platelets and red blood cells appear with a low frequency, and substantially return to the baseline position of the volume histogram. As shown in FIG. 4B, in the volume histogram of the abnormal blood sample containing at least one type of large platelets, schistocytes and microcytes, it is hard to clearly differentiate the detection peak of platelets from that of red blood cells. If the foregoing volume boundary value of platelets and red blood cells is used, particles corresponding to the volume boundary value appear with a relatively high frequency, and are far from the baseline position of the volume histogram. Those skilled in the art should understand that, volumes of large platelets, schistocytes and/or microcytes are between volumes of platelets and red blood cells, and the three types of blood cells with similar volumes are hard to be differentiated by using the electrical impedance detection method. Therefore, even the abnormal blood sample can be identified by the electrical impedance volume histogram (or various characteristic parameters of platelets/red blood cells), it is unable to identify which one or more types of large platelets, schistocytes and microcytes are contained in the abnormal blood sample.

Figure 5:
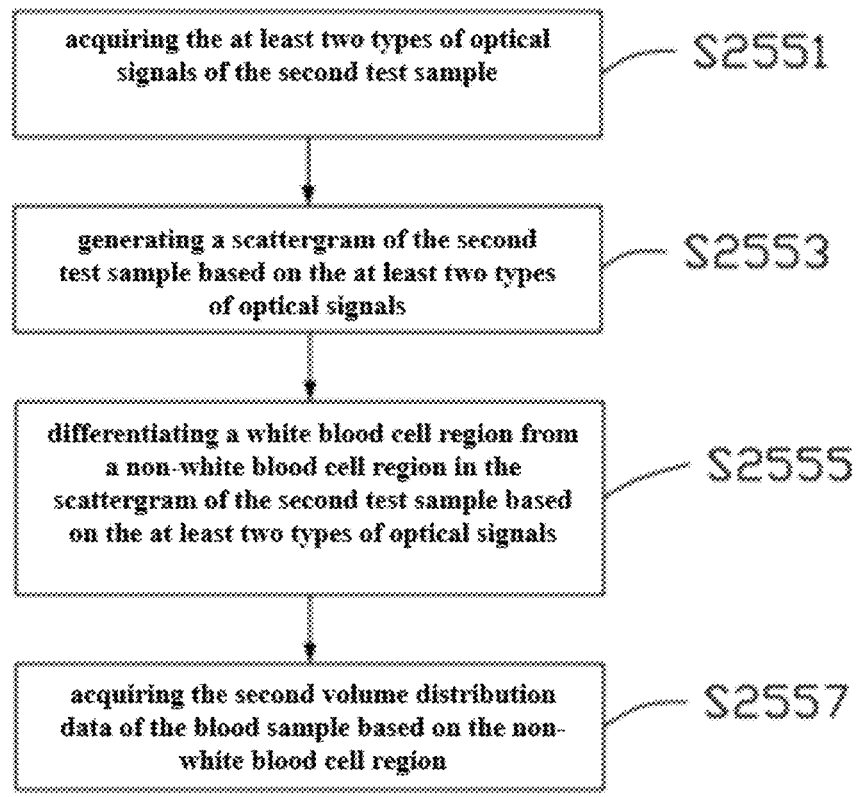
FIG. 5 is a flowchart of a method for acquiring second volume distribution data provided by the present disclosure.

At step S255, the present disclosure discloses a method for acquiring the second volume distribution data based on at least the forward scattered light signals of the second test sample. In the first aspect of the present disclosure, red blood cells in the second test sample are lysed and blood cells are stained by the fluorescence dye, and the at least two types of optical signals include forward scattered light signals and fluorescent signals. Specifically, please refer to FIG. 5, step S255 may include the following steps.

Step S2551: acquiring the at least two types of optical signals of the second test sample. Accordingly, for the blood analysis system in the first exemplary implementation, the signal acquisition module 750 acquires the at least two types of optical signals of the second test sample.

Step S2553: generating a scattergram of the second test sample based on the at least two types of optical signals. Accordingly, for the blood analysis system in the first exemplary implementation, the classification and counting module 770 generates a scattergram of the second test sample. In an embodiment shown in FIG. 6A, based on intensities of the forward scattered light signals and the fluorescent signals of the second test sample, an FL-FSC two-dimensional (2D) scattergram can be acquired. In an alternative implementation, the at least two types of optical signals acquired at step S235 include forward scattered light signals, side scattered light signals and fluorescent signals, and the scattergram generated at step S2553 may also be an FSC-SSC scattergram, an FL-SSC scattergram, or an FL-FSC-SSC three-dimensional (3D) scattergram. It can be understood that, when the at least two types of optical signals further include other optical signals (such as medium-angle scattered light and fluorescent signals), the scattergram may be 2D or 3D scattergrams of other forms. It can be understood that, the abscissa and ordinate of the scattergram may also be other parameters of forward scattered light signals and side scattered light signals that reflect particle characteristics of the first test sample, and the abscissa and ordinate of the scattergram may also be non-linear coordinate axis, such as logarithmic coordinate axis, to further highlight differences in distribution among particle populations.

Step S2555: differentiating a white blood cell region from a non-white blood cell region in the scattergram of the second test sample based on the at least two types of optical signals. Accordingly, for the blood analysis system in the first exemplary implementation, the classification and counting module 770 differentiates a white blood cell region from a non-white blood cell region in the scattergram of the second test sample based on the at least two types of optical signals. Taking the embodiment shown in FIG. 6A as an example, the white blood cell region W and the non-white blood cell region P can be differentiated from each other in the scattergram based on differences in intensities of the forward scattered light signals and the fluorescent signals of the second test sample. The white blood cell region W includes a region where white blood cells appear in the scattergram. The non-white blood cell region P includes a region where platelets and/or impurity particles after hemolysis appear in the scattergram. Those skilled in the art should understand that, the white blood cell region W and the non-white blood cell region P may be set by using gating technique.

Please refer to FIG. 4A, in the prior art, it is generally believed that, in particle populations characterized by an optical scattergram of a hemolyzed blood sample, the particle population with relatively small scattered light intensities and fluorescence intensities mainly includes schistocytes and platelets. The inventors have found after repeated assumptions and experiments that at least part of platelets treated by a hemolytic agent differ in volume size and cellular content from schistocytes and white blood cells, which can be identified by an optical method.

Figure 6A:
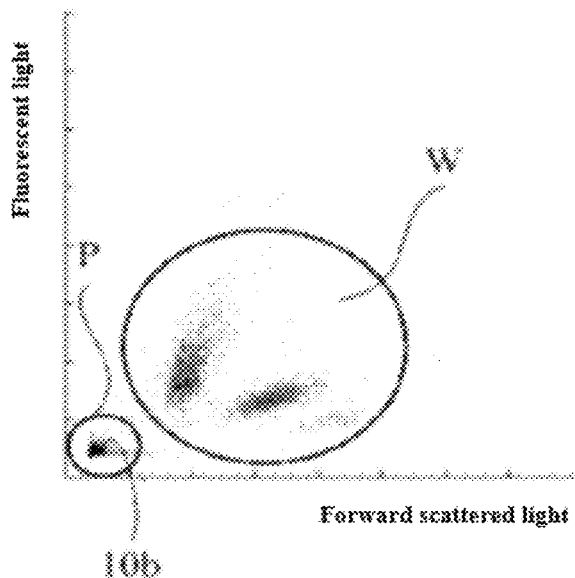
FIG. 6A is a scattergram generated by an embodiment of a second exemplary implementation of the present disclosure.
Figure 6B:
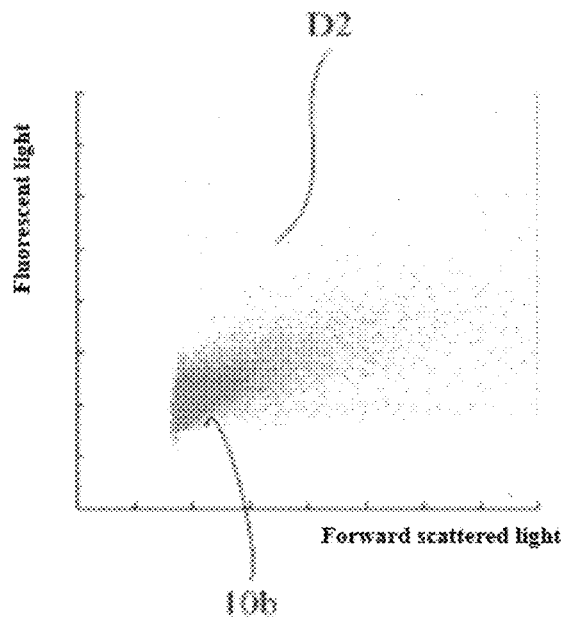
FIG. 6B is a partially enlarged view of the non-white blood cell region P in FIG. 6A.

In the second exemplary implementation, as shown in FIG. 6A, in the fluorescence (SFL or FL)-forward scattered light (FSC) scattergram acquired from the second test sample of the blood sample, the non-white blood cell region P and the white blood cell region W can be clearly differentiated from each other. The intensities of the forward scattered light signals of the non-white blood cell region P are substantially less than that of the white blood cell region W. The intensities of the fluorescent signals of the non-white blood cell region P are substantially less than that of the white blood cell region W. The non-white blood cell region P corresponds to the position of platelets 10b in the second test sample in the scattergram. FIG. 6B is a partially enlarged view of FIG. 6A, which is acquired by enlarging 2D distribution of platelets 10b in the non-white blood cell region P in the scattergram shown in FIG. 6A. The 2D distribution of the platelets 10b is a form of the second volume distribution data D2 acquired from the scattered light signals and the fluorescent signals of platelets in the second test sample.

Step S2557: acquiring the second volume distribution data of the blood sample based on platelets 10b in the non-white blood cell region P. Accordingly, for the blood analysis system in the first exemplary implementation, the classification and counting module 770 acquires the second volume distribution data D2 of the blood sample based on the platelets 10b in the non-white blood cell region P.

In an implementation, at step S2557, the second volume distribution data D2 of the test blood sample is acquired based on the forward scattered light signals of a particle population characterized by the platelets 10b in the non-white blood cell region P.

Specifically, in an embodiment, the volume (Vol) of each particle characterized by the platelets 10b in the non-white blood cell region P may be calculated by using Equation (1):

$$Vol_a = \alpha * FSC \qquad \text{Equation (1)}$$

wherein, FSC is the intensity of forward scattered light signal of each particle (also referred to as "individual event") characterized by the platelets 10b in the non-white blood cell region P, and α is a constant.

Specifically, in another embodiment, the volume (Vol) of each particle characterized by the platelets 10b in the non-white blood cell region P may be calculated by using Equation (2):

$$Vol_b = \beta * \exp(\gamma * FSC) \qquad \text{Equation (2)}$$

wherein, FSC is the intensity of forward scattered light signal of each individual event characterized by the platelets 10b in the non-white blood cell region P, and β and γ are constants.

Specifically, in another embodiment, the volume (Vol) of each particle characterized by the platelets 10b in the non-white blood cell region P may be calculated by using Equation (3):

$$Vol_c = [1/(FSC * \sigma(2\pi)^{1/2})] \exp(-(\ln FSC - \mu)^2/2\sigma^2) \qquad \text{Equation (3)}$$

wherein, FSC is the intensity of forward scattered light signal of each individual event characterized by the platelets 10b in the non-white blood cell region P, and μ and σ are constants.

Figure 6C:
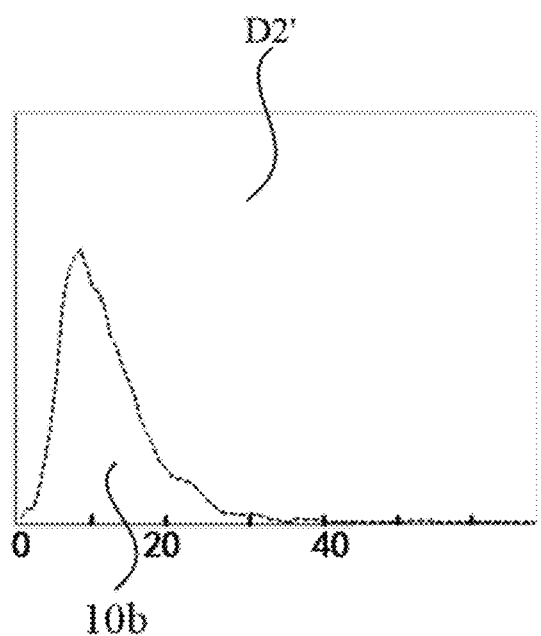
FIG. 6C is a derived volume histogram acquired based on the non-white blood cell region P in FIG. 6A.

At step S2557, volume distribution data related to platelets may be acquired based on the volume (Vol) of each particle of the particle population characterized by the platelets 10b in the non-white blood cell region P and a corresponding number of particles. Further, a volume distribution curve, which is referred to as derived volume histogram herein, may be acquired based on the volume distribution data of the non-white blood cell region P, as shown in FIG. 6C, D2' shown in FIG. 6C is one-dimensional (1D) distribution of the platelets in the second test sample. Herein, the volume distribution data (or derived volume histogram mentioned above) of the non-white blood cell region P is regarded as a form of the second volume distribution data D2.

Further, particles with a larger volume can be differentiated from particles with a smaller volume in the derived volume histogram by using a preset derived volume separation threshold, wherein the derived volume separation threshold may be selected from values between 10-20 fL, such as 10 fL, 12 fL, 15 fL or 20 fL. The inventors have found after repeated assumptions and experiments that the larger particles are mainly part of platelets with a relatively large volume in the test blood sample, for example, large platelets. Therefore, a derived volume distribution histogram of the larger platelets in the blood sample can be acquired, in which particles have a volume greater than the derived volume separation threshold. Alternatively, a count value of this part of platelets can further be acquired based on the derived volume distribution histogram of the larger platelets. It can be understood that, when the derived volume separation threshold is set as a volume boundary value for differentiating large platelets, volume distribution information of large platelets and/or a count value of large platelets in the test blood sample and the like can be acquired in the second exemplary implementation.

EXAMPLES

A plurality of blood samples was detected by respectively executing the analysis method provided by the present disclosure and a reference method of the prior art in a BC-6800 blood cell analyzer produced by SHENZHEN MINDRAY BIO-MEDICAL ELECTRONICS CO., LTD. By comparing counts of large platelets obtained by the method provided by the present disclosure with that obtained by the reference method, the correlations therebetween were obtained.

The steps of the reference method were as follows:

A blood samples was mixed and reacted with a reagent to obtain a test solution, and the components of the reagent were as follows:

| | |
|---|---|
| Fluorescence dye | 7 mg |
| $NaH_2PO_4 \cdot H_2O$ | 53.8 mg |
| $Na_2HPO_4 \cdot 7H_2O$ | 163.4 mg |
| Cocamidopropyl betaine | 100 mg |
| Dissolved in 1 L water, pH was 7 | |

The structural formula of the fluorescence dye was

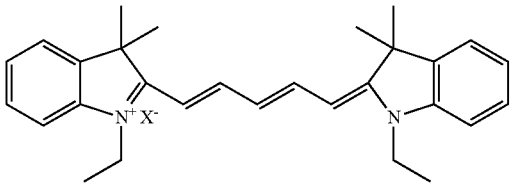

Forward scattered light signals, side scattered light signals and fluorescent signals of each cell in the test solution were detected by the BC-6800, and platelets were identified using the forward scattered light signals and the fluorescent signals, a total number of platelets was thus acquired. Based on the forward scattered light signals and the side scattered light signals of platelet particles, the volume of each platelet can be calculated by using the Mie Scattering Theory (ZHANG Wei, LU Yuan, DU Shiming, et. al., Analysis on Mie Scattering Characteristics of Spherical Particles, Optical Technology, November 2010: Volume 36 Issue 6: 936-939.), thereby acquiring numbers of platelets with different volumes. A ratio of large platelets was acquired according to the number of large platelets and the total number of platelets.

Specifically, 82 blood samples were selected to compare the method of the present disclosure and the reference method. Among the 82 blood samples, there were 57 normal blood samples, 15 samples containing red blood cell fragments, 5 samples containing microcytes and 5 samples containing large platelets, which was confirmed by manual microscopic examination. According to the method of the present disclosure, as shown in FIG. 6A, FIG. 6B and FIG. 6C, a volume histogram of platelets subjected to hemolysis was acquired by Equation (1), and information about platelets was calculated.

Figure 14A:
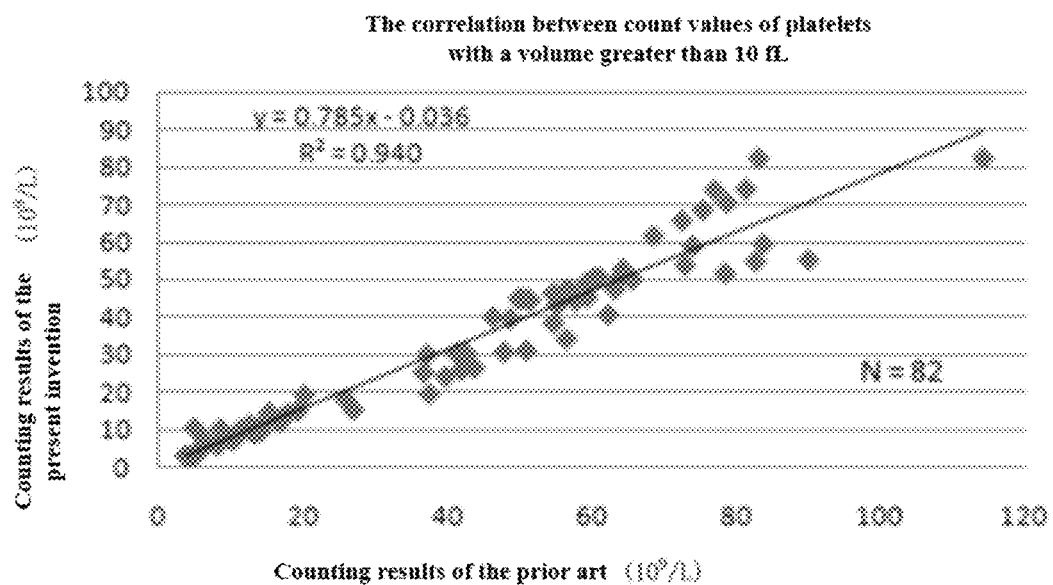
FIG. 14A shows a correlation between a count value of large platelets with a volume greater than 10 fL acquired by an implementation of the present disclosure and a count value of large platelets with a volume greater than 10 fL acquired by the prior art.

FIG. 14A shows a correlation between a count value of large platelets with a volume greater than 10 fL acquired by the implementation and a count value of large platelets with a volume greater than 10 fL acquired by the prior art. In the linear regression analysis of two detection results of the 82 blood samples, the correlation coefficient R2 was 0.940, indicating a good correlation between the method of the present disclosure and the reference method, and the implementation provided by the present disclosure can substantially accurately acquire the count of large platelets with a volume greater than 10 fL.

Figure 14B:
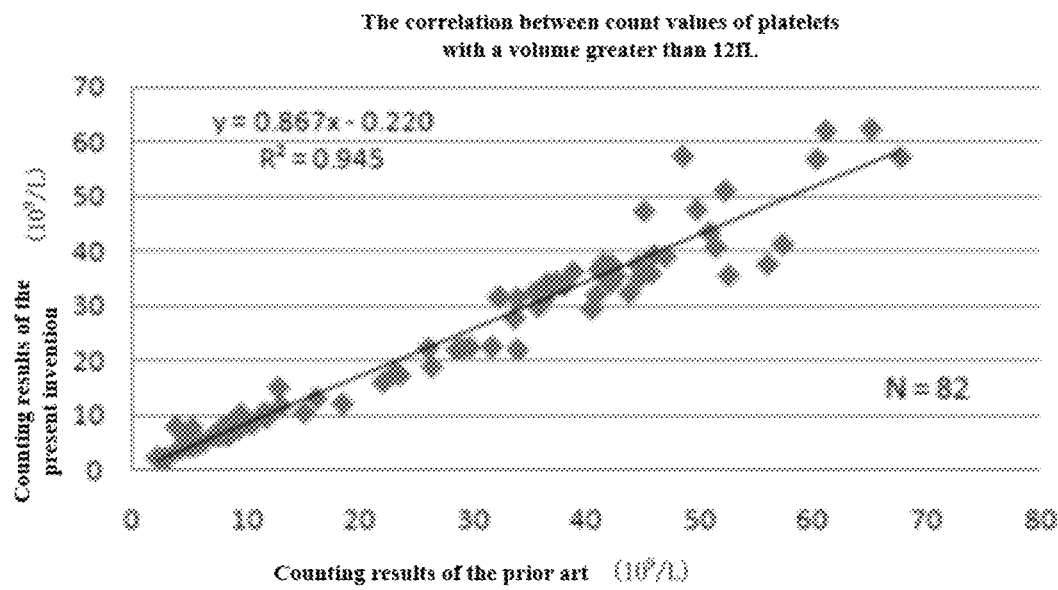
FIG. 14B shows a correlation between a count value of large platelets with a volume greater than 12 fL acquired by the implementation and a count value of large platelets with a volume greater than 12 fL acquired by the prior art.

FIG. 14B shows a correlation between a count value of large platelets with a volume greater than 12 fL acquired by the implementation and a count value of large platelets with a volume greater than 12 fL acquired by the prior art. In the linear regression analysis of two detection results of the 82 blood samples, the correlation coefficient R2 was 0.945, indicating a good correlation between the method of the present disclosure and the reference method, and the implementation provided by the present disclosure can substantially accurately acquire the count of large platelets with a volume greater than 12 fL.

Figure 14C:
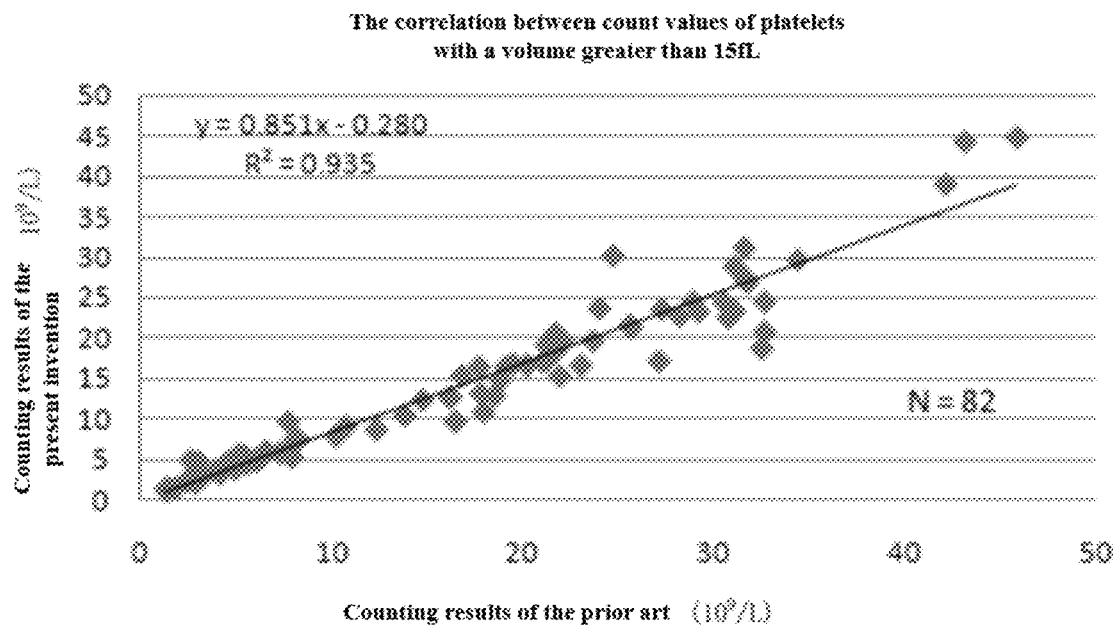
FIG. 14C shows a correlation between a count value of large platelets with a volume greater than 15 fL acquired by the implementation and a count value of large platelets with a volume greater than 15 fL acquired by the prior art.

FIG. 14C shows a correlation between a count value of large platelets with a volume greater than 15 fL acquired by the implementation and a count value of large platelets with a volume greater than 15 fL acquired by the prior art. In the linear regression analysis of two detection results of the 82 blood samples, the correlation coefficient R2 was 0.935, indicating a good correlation between the method of the present disclosure and the reference method, and the implementation provided by the present disclosure can substantially accurately acquire the count of large platelets with a volume greater than 15 fL.

Figure 14D:
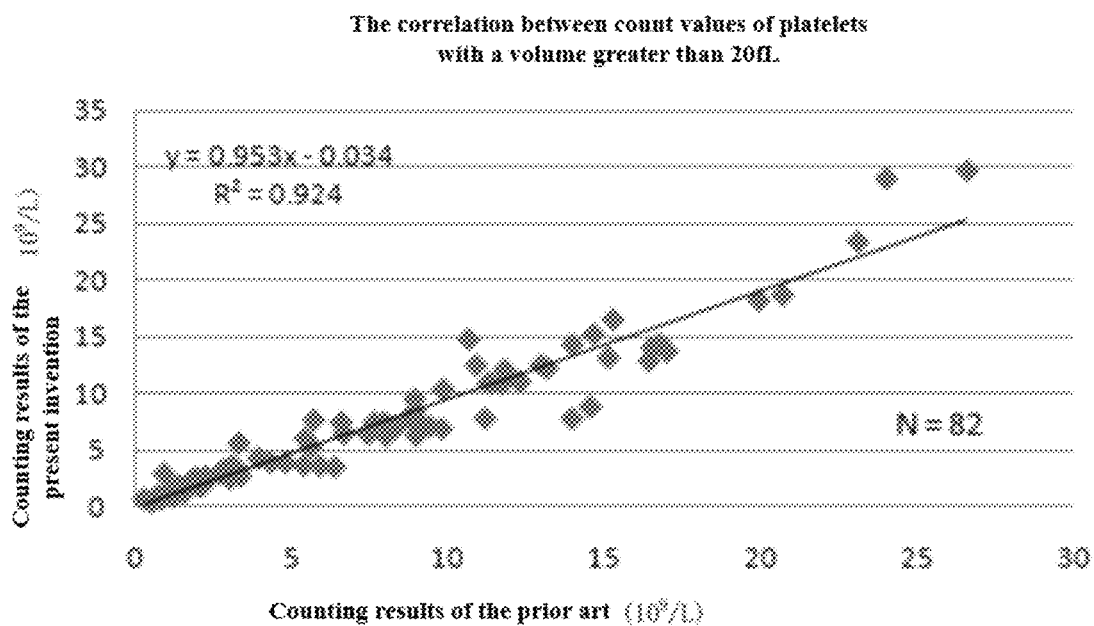
FIG. 14D shows a correlation between a count value of large platelets with a volume greater than 20 fL acquired by the implementation and a count value of large platelets with a volume greater than 20 fL acquired by the prior art.

FIG. 14D shows a correlation between a count value of large platelets with a volume greater than 20 fL acquired by the implementation and a count value of large platelets with a volume greater than 20 fL acquired by the prior art. In the linear regression analysis of two detection results of the 82 blood samples, the correlation coefficient R2 was 0.924, indicating a good correlation between the method of the present disclosure and the reference method, and the implementation provided by the present disclosure can substantially accurately acquire the count of large platelets with a volume greater than 20 fL.

In an alternative implementation, the at least two types of optical signals acquired at step S235 include forward scattered light signals, side scattered light signals and fluorescent signals. Then, at step S2557, based on the forward scattered light signals and the side scattered light signals of the non-white blood cell region P, the volume of each particle in the non-white blood cell region P may be calculated by using the Mie Scattering Theory (ZHANG Wei, LU Yuan, DU Shiming, et. al., Analysis on Mie Scattering Characteristics of Spherical Particles, Optical Technology, Noveber 2010: Volume 36 Issue 6: 936-939.), thereby acquiring volume distribution data of the particle population characterized in the non-white blood cell region P, that is, the second volume distribution data. Alternatively, a derived volume histogram may be acquired based on the volume distribution data of the non-white blood cell region P. Alternatively, a curve portion of larger particles in the derived volume histogram may be acquired based on the derived volume histogram and a derived volume separation threshold, and information of the larger platelets in the test blood sample, such as a count value, may be acquired based on the curve portion. It can be understood that, when the derived volume separation threshold is set as a volume boundary value for differentiating large platelets, according to the second exemplary implementation, volume distribution information of large platelets and/or a count value of large platelets, etc. in the test blood sample may be acquired. Obviously, in the alternative implementation, the second volume distribution data may also be acquired by using Equation (1), Equation (2) or Equation (3) based on the forward scattered light signals of the non-white blood cell region P.

The second volume distribution data of the test blood sample may be acquired by sequentially executing steps S2551-S2557 in step S255. Since red blood cells in the second test sample in the present disclosure are lysed, the second volume distribution data substantially does not contain information related to microcytes. Further, red blood cells and schistocytes in the second test sample are substantially lysed, thereby acquiring volume distribution information of large platelets and the like using one or more types of the at least two types of optical signals. As can be seen from the above, the first volume distribution data described in the present disclosure may contain information about large platelets, microcytes and/or schistocytes. Therefore, whether the test blood sample contains microcytes or schistocytes or not can be determined by comparing the first volume distribution data with the second volume distribution data.

Figure 7A:
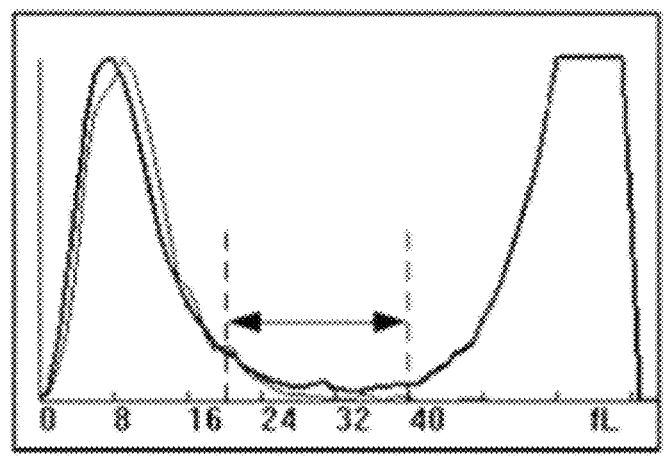
FIG. 7A is a schematic diagram showing difference between impedance graphs of first and second volume distribution data of a normal blood sample.
Figure 7B:
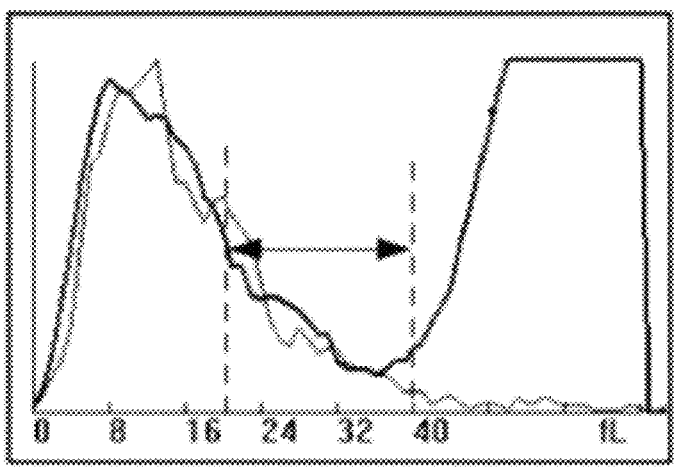
FIG. 7B is a schematic diagram showing difference between impedance graphs of first and second volume distribution data of a large platelet sample.
Figure 7C:
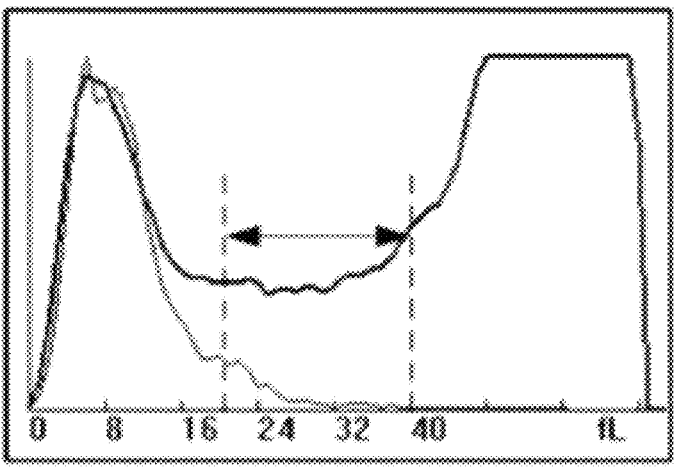
FIG. 7C is a schematic diagram showing difference between impedance graphs of first and second volume distribution data of a schistocyte sample.

In another implementation, whether curves are different or not may be determined by comparing similarity (or dissimilarity) of two impedance graphs. For example, a comparison result may be acquired by comparing graph portions in the same cell volume interval (that is, same abscissa interval (the same abscissa interval is represented by an interval between two coordinate points formed by two dashed lines at vertical direction intersecting abscissa axis in FIG. 7A, FIG. 7B and FIG. 7C)) of two impedance graphs reflecting the first and second volume distribution data shown in FIG. 7A, FIG. 7B, FIG. 7C by using an image comparison technique. For a normal blood sample, the comparison result acquired by comparing impedance graphs of the first and second volume distribution data is "similar" (as shown in FIG. 7A). For a large platelet sample, the comparison result acquired by comparing impedance graphs of the first and second volume distribution data is "similar" (as shown in FIG. 7B). For a schistocyte sample, the comparison result acquired by comparing impedance graphs of the first and second volume distribution data is "dissimilar" (as shown in FIG. 7C). It should be understood that whether the blood sample is a microcyte sample is determined based on the red blood cell detection data, and whether the two impedance graphs are similar or not is determined by comparing the impedance graphs of the first and second volume distribution data. When the blood sample is not a microcyte sample, and the comparison result acquired by comparing the impedance graphs of the first and second volume distribution data is "dissimilar", it can be determined that the blood sample may contain schistocytes.

In the present disclosure, at step S257, the red blood cell detection data of the blood sample is acquired. The acquired red blood cell detection data are mainly used for analyzing whether the blood sample contains microcytes. Those skilled in the art should understand that, the red blood cell detection data of the blood sample may be acquired by the electrical impedance signals mentioned above, or by other detection methods (for example, by detecting a non-hemolyzed blood sample using an optical method). Specifically, in an embodiment, the method for determining whether the blood sample contains microcytes using the electrical impedance signals may include: acquiring a volume distribution histogram of red blood cells by using the electrical impedance method, and calculating a mean value of the volume distribution histogram of red blood cells, wherein the mean value is mean corpuscular volume (MCV). It should be understood that, red blood cells with an MCV less than 80 fL can generally be regarded as microcytes. When the MCV acquired by using the method is less than 80 fL, it can be determined that the blood sample contains microcytes. Specifically, in another embodiment, volume distribution information of above 20% of the volume distribution histogram of red blood cells is acquired by the electrical impedance method, and a mean value of the above 20% volume distribution information is calculated, wherein the mean value is MCV. Specifically, in another embodiment, whether the blood sample contain microcytes may also be determined by the optical method, including: a volume of a single red blood cell is calculated by using scattered light of the single red blood cell, and then a mean volume of all red blood cells is acquired. The volume of a single red blood cell may be expressed by the following equation:

Volume of a single red blood cell=$f$ (SSC, FSC of a single red blood cell), wherein $f$ represents a function.

In an embodiment, for a method for calculating the volume of a single red blood cell, reference may be made to U.S. Pat. No. 5,633,167, the entire disclosure of which is incorporated herein by reference.

The red blood cell detection data includes but not limited to volume distribution data of red blood cells and related characteristic parameters of red blood cells. In a specific implementation, the red blood cell detection data may be MCV. The MCV may be acquired by calculating a mean value of a volume histogram of red blood cells acquired by using the electrical impedance detection method, or by calculating a mean value of a histogram by using volume distribution information of above 20% of a volume histogram peak of red blood cells acquired by the electrical impedance detection method, or by calculating a volume of a single red blood cell based on its scattered light and then calculating MCV. For the method for calculating the volume of a single red blood cell by using scattered light, reference may be made to U.S. Pat. No. 5,633,167.

In another specific implementation, the red blood cell detection data may be a red blood cell volume at a preset percentage quantile acquired based on the volume distribution data of red blood cells, for example, a red blood cell volume at 20% quantile, 30% quantile, 60% quantile or 80% quantile.

In the second exemplary implementation, at step S270, whether the test blood sample may contain schistocytes is determined based on the first volume distribution data, the second volume distribution data and the red blood cell detection data. Accordingly, for the blood analysis system in the first exemplary implementation, the alarm module 790 determines whether the test blood sample may contain schistocytes based on the first volume distribution data, the second volume distribution data and the red blood cell detection data. As can be seen from the above, the first volume distribution data acquired by the electrical impedance detection method may contain information about one or more types of large platelets, microcytes or schistocytes, and the second volume distribution data acquired by the method of the present disclosure can provide information about large platelets. Thus, at step S270, whether the test blood sample contains microcytes or schistocytes or not is determined based on the first volume distribution data and the second volume distribution data, whether the test blood sample contains microcytes is determined based on the red blood cell detection data, and then whether the test blood contains schistocytes is determined based on the above two determination results.

Figure 8A:
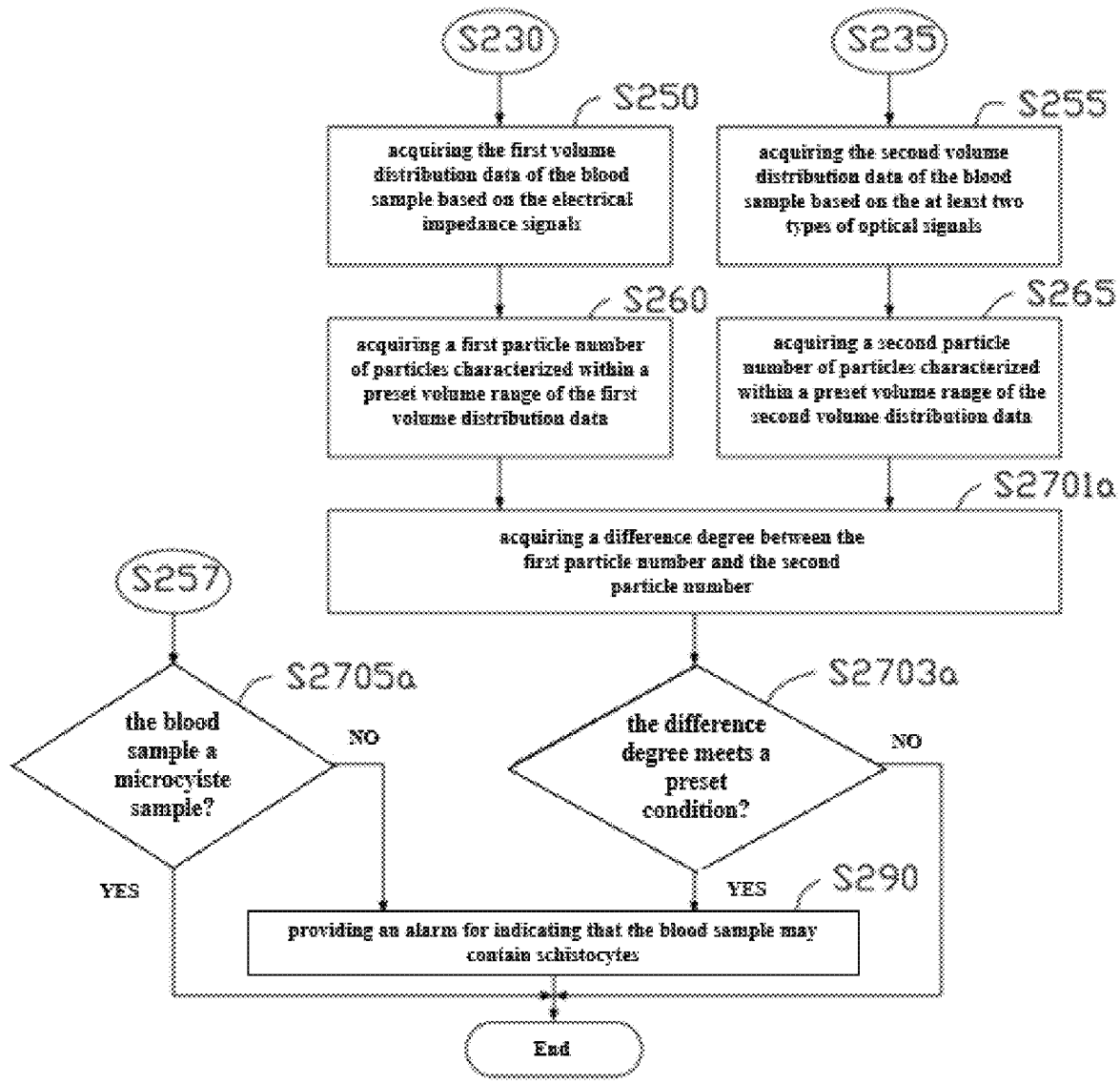
FIG. 8A is a flowchart of part of steps of an implementation of the blood analysis method provided by the present disclosure.

It can be understood that, in order to compare the first volume distribution data and the second volume distribution data, volume distribution data within the same volume range or derived volume range is selected for comparison. The volume distribution used for comparison may be an area (that is, the number of particles) of a volume distribution curve within the volume range. FIG. 8A shows an implementation of a flowchart of part of steps for alarming a schistocyte sample in the exemplary implementation provided by the present disclosure. After step S250, a first particle number of particles characterized within a preset volume range is acquired at step S260 based on the first volume distribution data. The preset volume range may be between a volume value corresponding to a peak characterizing platelet and a volume value corresponding to a peak characterizing red blood cells in electrical impedance volume histogram. Specifically, the preset volume range may be 10-50 fL, 15-45 fL or 20-40 fL. Those skilled in the art should understand that, the preset volume range may be a volume interval characterizing large platelets microcytes or schistocytes in the electrical impedance volume distribution. Accordingly, after step S255, a second particle number of particles characterized within the preset volume range is acquired at step S265 based on the second volume distribution data. The second volume distribution data may be the derived volume histogram mentioned above. It can be understood that, a same or similar preset volume range is used at steps S260 and S265 to quantitatively compare the first particle number and the second particle number in subsequent steps.

At step S2701a, a difference degree between the first particle number and the second particle number is calculated. Then, whether the difference degree meets a preset condition is determined at step S2703a. It can be understood that, if the first particle number is significantly greater than the second particle number, the test blood sample may contain microcytes or schistocytes. It can be understood that, in other implementations, at step S2701, a shape difference between the first volume distribution curve and the second volume distribution curve within the preset volume range may also be acquired, and it can also be reflected that the test blood sample may contain microcytes or schistocytes when the first volume distribution curve has a significant convex within the preset volume range compared to the second volume distribution curve.

In the implementation, at step S2701a, the first particle number and the second particle number may be calculated using a mathematical expression to obtain an evaluation value (EV) that reflects the difference degree therebetween. It should be noted that the EV may be a difference degree of the second volume distribution data relative to the first volume distribution data, or a difference degree of the first volume distribution data relative to the second volume distribution data. The EV may be a difference or a quotient between the second particle number N2 and the first particle number N1, or may be a reciprocal, a multiple or an exponent of their difference or quotient. In an embodiment, $EV=a*(N2/N1)$, where a is a preset coefficient. In another embodiment, $EV=b*(N1/N2)$, where b is a preset coefficient. In another embodiment, $EV=(N1-N2)c$, where c is a preset coefficient. In another embodiment, $EV=d*(N1-N2)$, where d is a preset coefficient. The EV may also be other values that can reflect the difference between PLT1 and PLT2, for example, $EV=(N1-N2)/N1$, $EV=(N1-N2)/N2$, etc.

At step S2703a, whether the difference degree acquired at step S2701a meets a preset condition is determined. In an embodiment, the preset condition may be a preset threshold, and the acquired EV is compared with the preset threshold at step S2703a, thereby acquiring an evaluation result that the evaluation value is greater than, equal to or less than the preset threshold. It can be understood that, the preset threshold at step S2703a is set according to a setting mode of the EV, and the preset threshold is used to analyze whether the first particle number is significantly larger than the second particle number.

When the determination result at step S2703a is yes, that is, the difference degree meets the preset condition, it is indicated that the test sample may be a microcyte or schistocyte sample, and the process continues. When the determination result at step S2703a is no, that is, the difference degree does not meet the preset condition, it is indicated that the test sample is not a microcyte or schistocyte sample, and the process ends.

At step S2705a, whether the test blood sample is a microcyte sample is determined based on the red blood cell detection data acquired at step S257. Those skilled in the art should understand that, when the red blood cell detection data is a mean volume of red blood cells, if the mean volume of red blood cells is small, the test blood sample may be a microcyte sample, for example, a sample having an MCV less than 80 fL is regarded as a microcyte sample. Therefore, whether the test blood sample is a microcyte sample may be determined by comparing the mean volume of red blood cells with a preset mean volume threshold of red blood cells. When the red blood cell detection data is a red blood cell volume at a certain preset percentage quantile of red blood cell distribution volume, if the volume is not less than expected, the test blood sample may be a microcyte sample. For example, if the red blood cell volume at 80% quantile in the volume distribution data of normal red blood cells is 100 fL, and the red blood cell volume at 80% quantile in the volume distribution data of red blood cells in a certain sample is 95 fL, the sample can be determined as a microcyte sample. On the contrary, if the red blood cell volume at 20% quantile in the volume distribution data of normal red blood cells is 70 fL, and the red blood cell volume at the same quantile in the volume distribution data of red blood cells in a certain sample is 60 fL, the sample can also be determined as a microcyte sample. Therefore, whether the test blood sample is a microcyte sample may also be determined by comparing a volume at a preset volume percentage quantile of red blood cells with a preset volume threshold. Preferably, the preset volume percentage of red blood cells is a volume at a lower percentage quantile, such as 5-30%, thereby more effectively reflecting information about microcytes in the test blood sample.

When the determination result at step S2705a is yes, that is, the test sample may be a microcyte sample, then the process ends. When the determination result at step S2705a is no, that is, the test sample is not a microcyte sample, then the process continues.

When the determination result at step S2703a is yes, that is, the test sample may be a microcyte or schistocyte sample. Moreover, when the determination result at step S2705a is no, that is, the test sample is not a microcyte sample, it is determined at step S270 that the test sample may be a schistocyte sample, and it is alarmed that the blood sample may contain schistocytes at step S290. If any process at step S2703a or S2705a ends, which means the determination result at step S270 is no, then the process ends. It can be understood that, in the flow of the implementation shown in FIG. 8A, determination steps S2703a and S2705a may be executed in parallel or in sequence.

Figure 8B:
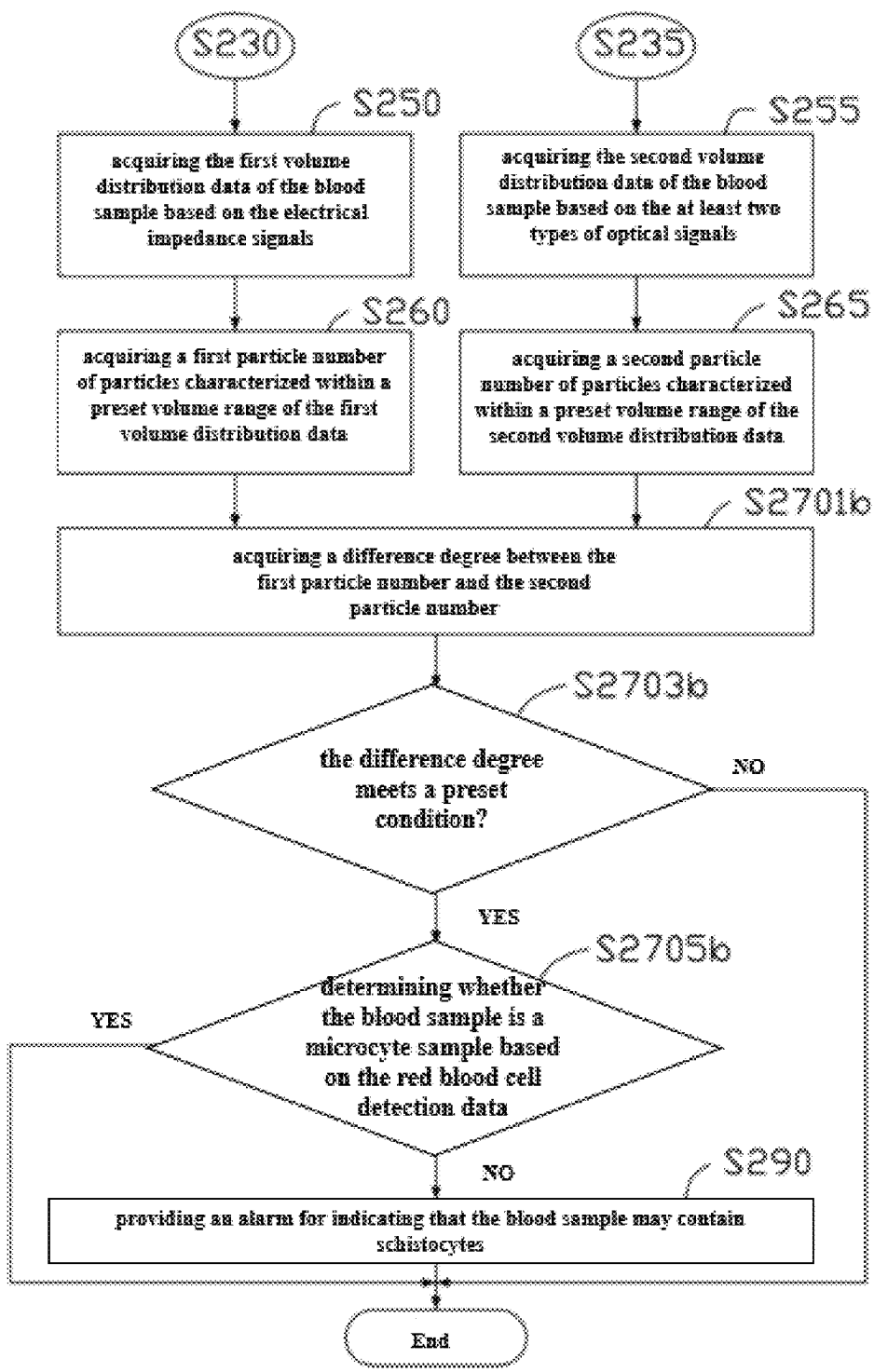
FIG. 8B is a flowchart of part of steps of another implementation of the blood analysis method provided by the present disclosure.

FIG. 8B shows another implementation of the flowchart of part of the steps for alarming a schistocyte sample in the exemplary implementation provided by the present disclosure. In the implementation shown in FIG. 8B, whether the difference degree between the first particle number and the second particle number meets a preset condition is determined at step S2703b. When the determination result at step S2703b is yes, then step S2705b is executed to determine whether the blood sample is a microcyte sample. When the determination result at step S2705b is no, S290 is executed to provide an alarm for indicating that the blood sample may contain schistocytes. Unlike the implementation shown in FIG. 8A, in this implementation, steps S2703b and S2705b are not independently executed, whether to execute step S2705b depends on the determination result at step S2703b.

It can be understood that, in other implementations, determination sequence of steps S2703b and S2705b may also be reversed. In other words, step S2705b is executed first, when the determination result at step S2705b is no, then step S2703b is executed. When the determination result at step S2703b is yes, step S290 is executed to provide an alarm for indicating that the blood sample may be an abnormal sample containing schistocytes.

In the second exemplary implementation, alternatively, a step of outputting other detection results and/or intermediate results may further be included. The detection results include but not limited to the first volume distribution data acquired at step S250, the second volume distribution data acquired at step S255 and the red blood cell detection data acquired at step S257. The intermediate results include but not limited to the scattergram acquired at step S255, the non-white blood cell region in the scattergram, the derived volume histogram, the curve portion of the larger particles separated by the derived volume separation threshold value, and results acquired at each sub-step of step S270, etc.

A blood analysis method for alarming a blood sample containing schistocytes provided by a third exemplary implementation of the present disclosure will be described below. Compared with the method of the second exemplary implementation described above, in the third exemplary implementation, a different method at step S255 for acquiring the second volume distribution data is adopted. For the main analysis process and other steps of the third exemplary implementation, reference can be made to FIG. 3 and the contents described above, which will not be repeated here.

In the third exemplary implementation, the second volume distribution data is acquired based on at least two types of optical signals of the second test sample at step S255a, wherein the at least two types of optical signals include forward scattered light signals and fluorescent signals of the second test sample, red blood cells of which are lysed. Specifically, step S255a includes the following steps.

Step S2551a: acquiring the at least two types of optical signals of the second test sample.

Step S2553a: generating a scattergram of the second test sample based on the at least two types of optical signals.

Figure 9:
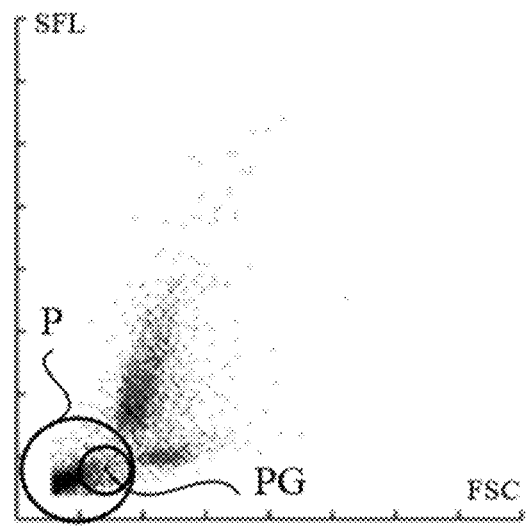
FIG. 9 is a schematic diagram of a designated region in a non-white blood cell region of a fluorescence-forward scattered light (SFL-FSC) scattergram of a second test sample of a blood sample according to an embodiment of a third exemplary implementation of the present disclosure.

Step S2555a: differentiating a white blood cell region from a non-white blood cell region in the scattergram of the second test sample based on the at least two types of optical signals. In the third exemplary implementation, the non-white blood cell region differentiated at step S2555a is a large platelet region PG. The large platelet region PG is a region where large platelets in the second test sample appear in the scatter diagram. In an embodiment shown in FIG. 9, the intensities of the forward scattered light signals of the large platelet region PG are substantially less than that of the white blood cell region W, and are substantially greater than that of schistocytes at the lower left corner of the scattergram. The intensities of the fluorescent signals of the large platelet region PG are substantially less than that of the white blood cell region W.

Step S2557a: acquiring the second volume distribution data of the blood sample based on the large platelet region PG. In the third exemplary implementation, the second volume distribution data may be detection data of large platelets, such as volume distribution data of large platelets, a count of large platelets or other characteristic parameters that can reflect volume distribution of large platelets.

In an implementation, at step S2557a, the volume distribution data of large platelets may be acquired based on the forward scattered light signals of a particle population characterized in the large platelet region PG, and a derived volume histogram of large platelets may be acquired based on the volume distribution data of large platelets. Specifically, the forward scattered light signals may be converted into a volume of each particle in the large platelet region PG by using Equation (1), Equation (2) or Equation (3), thereby acquiring the volume distribution data of large platelets. In another implementation of the third exemplary implementation, the at least two types of optical signals acquired at step S235a include forward scattered light signals, side scattered light signals and fluorescent signals, and the volume of each particle in the large platelet region PG may also be calculated at step S2557a based on the forward scattered light signals and the side scattered light signals of the particle population characterized in the large platelet region PG by using the Mie Scattering Theory, thereby acquiring the volume distribution data of large platelets. A derived volume histogram of large platelets may be acquired based on the volume distribution data of the large platelets.

The second volume distribution data of the test blood sample may be acquired by sequentially executing steps S2551a-S2557a in step S255a, and the second volume distribution data may be volume distribution data of large platelets. Further, a derived volume histogram of large platelets may be acquired by at least the forward scattered light signals, based on the volume distribution data of large platelets. As can be seen from the above, the first volume distribution data described in the present disclosure may contain information about large platelets, microcytes and/or schistocytes. An electrical impedance volume histogram may be acquired based on the first volume distribution data. Therefore, whether the test blood sample contains microcytes or schistocytes or not may be analyzed by comparing the electrical impedance volume histogram with the derived volume histogram of large platelets. For example, when the electrical impedance volume histogram corresponding to the first volume distribution data has a significant convex within a preset volume range compared with the derived volume histogram of large platelets corresponding to the volume distribution data of large platelets, the test blood sample may contain microcytes or schistocytes.

Alternatively, a count value of large platelets and/or other characteristic parameters reflecting the volume distribution of large platelets may further be obtained based on the volume distribution data of large platelets. In the present disclosure, a volume threshold for defining large platelets may be set by users, and the volume threshold may be any numerical value between 10-20 fL, for example, large platelets may be platelets with a volume greater than 10 fL, 12 fL, 15 fL or 20 fL. Those skilled in the art should understand that the range of the large platelet region PG may be accordingly changed based on the set volume threshold of large platelets. Alternatively, the characteristic parameters reflecting the volume distribution of large platelets, such as count value of large platelets and distribution width of large platelets, may further be obtained based on the volume distribution data of the large platelets.

In an implementation, a number of particles (or referred to as "event number") of the particle population characterized in the large platelet region PG may also be acquired at step S2557a, and a count value of large platelets may be acquired based on the number of particles. Specifically, an electrical impedance volume histogram may be generated based on the first volume distribution data, platelets may be differentiated from red blood cells in the volume histogram by a preset volume boundary value, and then a volume histogram of platelets, a volume histogram of red blood cells and characteristic parameters of platelets and red blood cells in the blood sample may be respectively acquired. Those skilled in the art should understand that, in a volume histogram of an abnormal blood sample containing at least one type of large platelets, schistocytes and microcytes, it is hard to clearly differentiate the detection peak of platelets from that of red blood cells. If the foregoing volume boundary value of platelets and red blood cells is used, particles corresponding to the volume boundary value appear with a relatively high frequency (as shown in the figure, a convex can be visually seen in the electrical impedance volume histogram), and are far from the baseline position of the volume histogram. Further, a count value of large platelets may be acquired based on the number of particles of the particle population characterized in the large platelet region PG, and whether the count value of large platelets is less than a preset value is determined. It can be understood that, if the count value of large platelets is less than the preset value, and there is a convex in the electrical impedance volume histogram generated based on the first volume distribution data, the test blood sample may contain microcytes or schistocytes. Further, since red blood cells in the second test sample in the present disclosure are lysed, the second volume distribution data substantially does not contain information related to microcytes, that is, the volume distribution data of large platelets substantially does not contain information related to microcytes. Therefore, whether the test blood sample contains schistocytes can be analyzed by analyzing the electrical impedance volume histogram corresponding to the first volume distribution data and the count value of large platelets.

It should be understood that, when there is no need to generate the derived volume histogram, a 2-dimentional scattergram generated by any two types of the fluorescence, the forward scattered light, the side scattered light (or medium-angle scattered light) may be used for differentiating the large platelet region. When it is necessary to generate the derived volume histogram, at least the forward scattered light signals are needed for differentiating the large platelet region.

In the third exemplary implementation, the count value of large platelets in the test blood sample, that is, the second particle number described above, may directly or indirectly be acquired at step S255a. Therefore, at step S260a after step S250, a first particle number is accordingly acquired based on the volume threshold for defining large platelets at step S255a. Thus, the first particle number and the second particle number correspond to the same or similar volume intervals and can be used for subsequent determination.

For other specific contents of the third exemplary implementation, reference can be made to the contents of the second exemplary implementation, which will not be repeated herein. Table 1 shows detection results of 100 blood samples detected respectively by using manual microscopic examination and the method of the third exemplary implementation of the present disclosure. The manual microscopic examination adopts the method in ICSH Recommendations for Identification, Diagnostic Value, and Quantitation of Schistocytes recommended by International Council for Standardization in Haematology (ICSH), and a blood sample with a schistocyte ratio >1 detected by the microscopy is defined as a positive sample containing schistocytes. As shown in Table 1, the results of alarming schistocyte samples by using the method of the present disclosure has a relatively high accuracy, and an alarm for indicating blood samples containing schistocytes can be more accurately provided.

TABLE 1

| Microscopy result | | Result of alarming schistocytes using the present method | | | |
|---|---|---|---|---|---|
| Positive | Negative | Number of true positives | Number of true negatives | Number of false positives | Number of false negatives |
| 30 | 70 | 29 | 69 | 4 | 2 |
| | | True positive rate | True negative rate | False positive rate | False negative rate |
| | | 93.3% | 94.3% | 5.7% | 6.7% |

Figure 10:
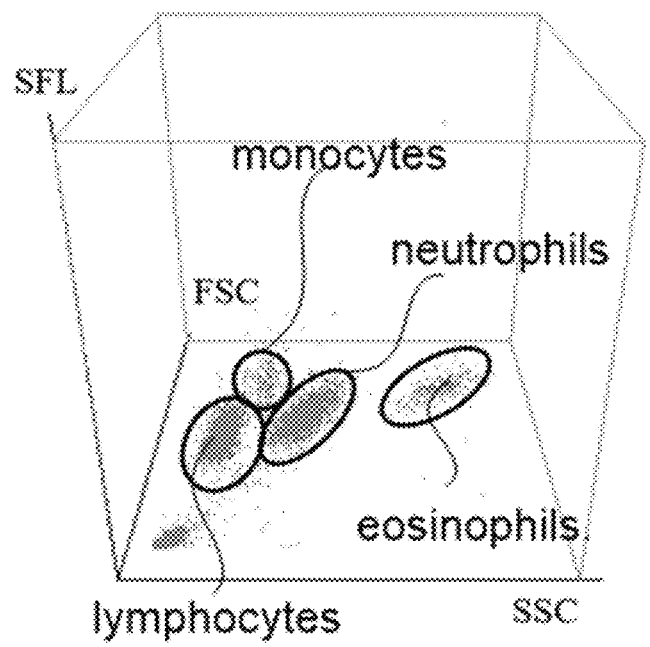
FIG. 10 is a fluorescence (SFL)-side scattered light (SSC)-forward scattered light (FSC) 3D scattergram of a second test sample of a blood sample for illustrating the differentiation of white blood cell subpopulations in an implementation of the present disclosure.
Figure 11:
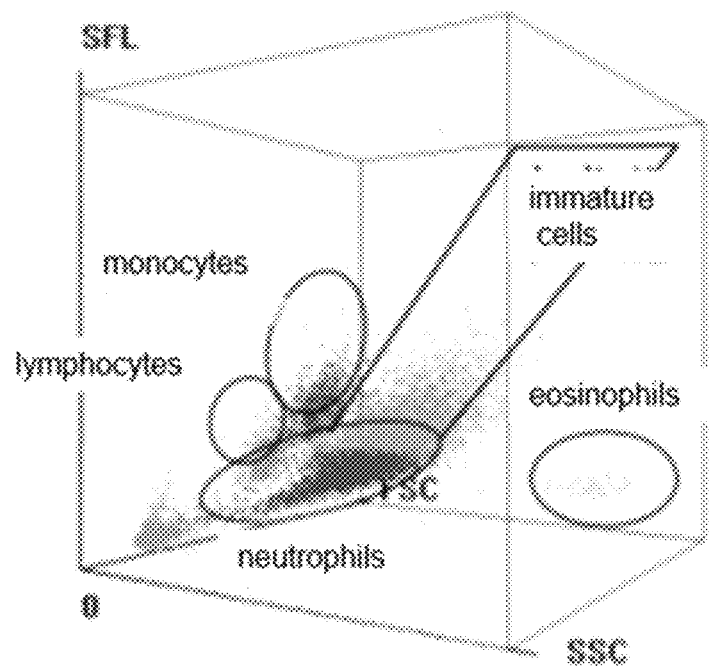
FIG. 11 is a side scattered light-forward scattered light (FSC-SSC) scattergram of a second test sample of a blood sample for illustrating the differentiation of immature cells in an implementation of the present disclosure.

Further, in some implementations, the present method may further include the step of differentiating white blood cells into their subpopulations by using the scattered light signals and the fluorescent signals of the second test sample. Main subpopulations of white blood cells include lymphocytes, monocytes, neutrophils, eosinophils and basophils. FIG. 10 shows an SFL-SSC-FSC 3D scattergram, and the white blood cells are differentiated into four subpopulations, namely lymphocytes, monocytes, neutrophils and eosinophils based on the fluorescent signals, the side scattered light signals and the forward scattered light signals of a test sample of a blood sample. Further, in other implementations, basophils in white blood cells may be differentiated from other white blood cell subpopulations based on the scattered light signals and the fluorescent signals of the test sample. In other embodiments, the present method may further include the steps of counting a number of white blood cells in the test sample and reporting the count of white blood cells in the blood sample. Those skilled in the art should understand that the present method may further include the step of identifying nucleated red blood cells, immature cells or blast cells based on the scattered light signals and the fluorescent signals of the test sample. For example, as shown in FIG. 11, when the blood sample contains immature cells, in the present method, based on the scattered light signals and the fluorescent signals of the second test sample, immature cells can be identified and white blood cells can be differentiated into four subpopulations, namely lymphocytes, monocytes, neutrophils and eosinophils.

Those skilled in the art should understand that all or part of the steps of the second or third exemplary implementation may be implemented by instructing related hardware of a blood analyzer through computer programs. The computer programs may be stored in a computer-readable storage medium and loaded into the blood analyzer having corresponding hardware system. When the computer programs are executed by a processor, the blood analyzer executes the analysis method for blood sample disclosed in the second or third exemplary implementation of the present disclosure.

The first aspect of the present disclosure further provides a blood analyzer. The blood analyzer includes a processor and a non-volatile computer-readable storage medium. The processor is configured to execute computer programs stored in the non-volatile computer-readable storage medium to implement the steps of the analysis method according to the second or third exemplary implementation.

The first aspect of the present disclosure further provides a non-volatile computer-readable storage medium storing computer programs thereon, wherein the computer programs, when executed by a processor, implement the steps of the analysis method of the second or third exemplary implementation. For the specific steps, reference can be made to various implementations and embodiments described above, which will not be repeated herein. Therefore, the analysis method of the second or third exemplary implementation may be implemented in the form of software function units and sold or used as an independent product.

The products and methods provided by the first aspect of the present disclosure can, based on the existing five-classification blood analysis system, respectively obtain detection data of red blood cells by using electrical impedance detection channel and hemolytic nucleated cell detection channel, such as white blood cell classification detection channel (for example, DIFF channel of BC-6800 blood analyzer produced by Shenzhen Mindray Bio-Medical Electronics Co., Ltd.) or nucleated red blood cell detection channel (for example, nucleated red blood cell channel of BC-6000 blood analyzer produced by Shenzhen Mindray Bio-Medical Electronics Co., Ltd.), and provide an alarm for indicating schistocyte samples by comparing the first and second volume distribution data of platelets acquired by the two detection channels. At the same time, a detection result of at least four types of white blood cells is acquired in the hemolytic white blood cell detection channel, or at least detection results of a count of nucleated red blood cells, a count of white blood cells, and identification of basophils are acquired in the nucleated red blood cell channel. Without using a separate detection channel, the products and methods provided by the first aspect of the present disclosure can provide users with more abundant detection information in a real time manner and can remind users to perform a reexamination or recheck on blood samples that may contain schistocytes without increasing the costs of the blood analysis system.

A second aspect of the present disclosure relates to a blood analysis method, system and storage medium based on electrical impedance signals and scattered light signals of a blood sample. Compared with the first aspect of the present disclosure, the second aspect of the present disclosure provides a product and method for giving an alarm for indicating that the blood sample may contain schistocytes, without using a fluorescence dye. It should be noted that in the second aspect of the present disclosure, a fluorescence dye may also be added to prepare a second test sample, and whether to use a fluorescence dye would not affect the realization of corresponding implementations.

A fourth exemplary implementation of the present disclosure provides a blood analysis method. Please refer to the flowchart of the steps shown in FIG. 3 again. The blood analysis method includes the following steps:

Step S200: providing a blood sample.

Step S220: mixing a first aliquot of the blood sample with a diluent agent to obtain a first test sample.

Step S225c: mixing a second aliquot of the blood sample with a lytic reagent to obtain a second test sample, wherein the lytic reagent includes a hemolytic agent for lysing red blood cells.

Step S230: detecting electrical impedance signals of the first test sample.

Step S235c: detecting at least two types of optical signals of the second test sample, wherein the at least two types of optical signals include first scattered light signals and second scattered light signals, the first scattered light signals are forward scattered light signals, and the second scattered light signals are at least one type of medium-angle scattered light signals and side scattered light signals.

Step S250: acquiring first volume distribution data of the blood sample based on the electrical impedance signals acquired at step S230.

Step S255c: acquiring second volume distribution data of the blood sample based on the at least two types of optical signals obtained at step S235.

Step S257: acquiring red blood cell detection data of the blood sample.

Step S270c: determining whether the blood sample may contain schistocytes based on the first volume distribution data, the second volume distribution data, and the red blood cell detection data.

If the determination result is yes, step S290 is executed to provide an alarm for indicating that the blood sample may contain schistocytes. If the determination result is no, the process ends.

Those skilled in the art should understand that all or part of the steps may be implemented by computer programs in combination with the blood analysis system shown in FIG. 1.

At step S225c, the second aliquot of the blood sample is mixed with the hemolytic agent to obtain the second test sample. The hemolytic agent may be any one of existing hemolytic agents used by automated blood analyzers for classifying white blood cells, and may be any one of a cationic surfactant, a nonionic surfactant, an anionic surfactant and an amphiphilic surfactant or any combination thereof.

At step S235c, the forward scattered light signals, and at least one type of the medium-angle scattered light signals and the side scattered light signals of the second test sample may be acquired by one or more optical detectors. The medium-angle scattered light signals may be detected by an optical detector at an angle between forward scattered light and side scattered light. The medium-angle scattered light signals may be low medium-angle scattered light signals detected at an angle range from about 8° to about 24° relative to an incident beam, or high medium-angle scattered light signals detected at an angle range from about 25° to about 65° relative to the incident beam. As mentioned above, the forward scattered light signals may be detected at an angle range from about 1° to about 10° relative to the incident beam, preferably, the forward scattered light signals may be detected at an angle range from about 2° to about 6° relative to the incident beam. The side scattered light signals may be detected at an angle of about 90° relative to the incident beam, alternatively, the side scattered light signals may also be detected at an angle range from about 65° to about 115° relative to the incident beam.

Similar to the method of the first aspect of the present disclosure, step S255c may include the following steps:

Step S2551c: acquiring the at least two types of optical signals of the second test sample, that is, the forward scattered light signals and at least one type of the medium-angle scattered light signals and the side scattered light signals.

Step S2553c: generating a scattergram of the second test sample based on the at least two types of optical signals.

Step S2555c: differentiating a white blood cell region from a non-white blood cell region in the scattergram acquired at step S2553c based on the at least two types of optical signals.

Step S2557c: acquiring the second volume distribution data of the blood sample based on the non-white blood cell region acquired at step S2555c.

In an implementation, similar to the second exemplary implementation described above, the non-white blood cell region P differentiated at step S2555c includes a region where platelets and/or impurity particles after hemolysis appear in the scattergram. At step S2557c, the forward scattered light signals of a particle population characterized in the non-white blood cell region P are converted into a volume of each particle in the non-white blood cell region P by using Equation (1), Equation (2) or Equation (3), thereby acquiring the second volume distribution data. When the second scattered light signals are the side scattered light signals, the volume of each particle in the non-white blood cell region P may also be acquired at step S2557c by using the Mie Scattering Theory based on the forward scattered light signals and the side scattered light signals of the particle population characterized in the non-white blood cell region P, thereby acquiring the second volume distribution data. The second volume distribution data may be represented in a numerical form or in a graphical form, such as a derived volume histogram.

Further, larger particles can be differentiated from smaller particles in the derived volume histogram by using a preset derived volume separation threshold. The derived volume separation threshold may be selected from values between 10-20 fL, such as 10 fL, 12 fL, 15 fL or 20 fL. In the separated derived volume histogram, a curve portion of the larger particles may also be regarded as a form of the second volume distribution data. Alternatively, characteristic parameters such as an area of the curve portion may also be acquired based on the curve portion of the larger particles in the derived volume histogram. The characteristic parameters may also be regarded as a form of the second volume distribution data.

Figure 12:
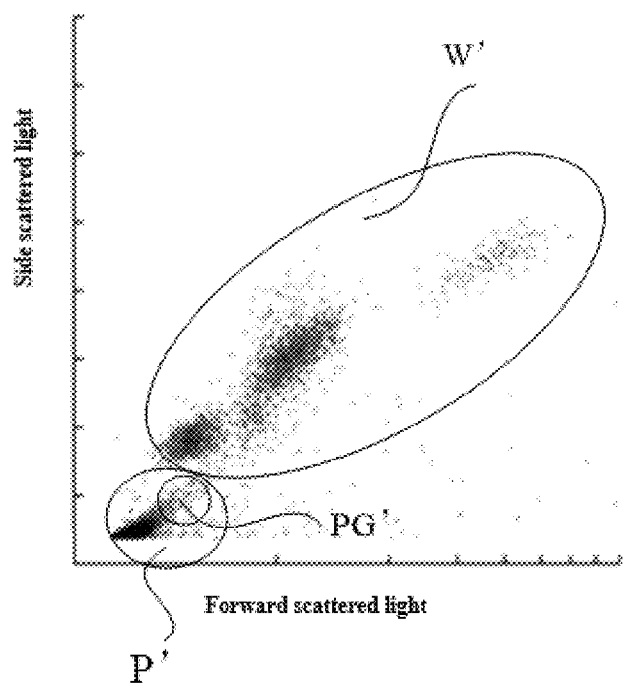
FIG. 12 is a forward scattered light-side scattered light (FSC-SSC) scattergram of a second test sample of an abnormal blood sample containing large platelets according to an embodiment of a fourth exemplary implementation of the present disclosure.

FIG. 12 shows an FSC-SSC scattergram generated by an embodiment of the implementation, in which P' is non-white blood cell region and PG' is large platelet region. At step S2557c, the scattered light signals of the particle population characterized in the large platelet region PG' may be converted into the volume of each particle in the large platelet region PG' by using Equation (1), Equation (2), Equation (3) or Mie Scattering Theory, thereby acquiring volume distribution data of large platelets. Alternatively, a derived volume histogram of large platelets may be acquired based on the volume distribution data of large platelets. Alternatively, characteristic parameters reflecting volume distribution of large platelets, such as a count value of large platelets, a distribution width of large platelets, etc., may also be obtained based on the volume distribution data of large platelets. Alternatively, at step S2557c, a count value of large platelets may also be acquired by acquiring a number of particles of the particle population characterized in the large platelet region PG'. It can be understood that, in the implementation, the second volume distribution data may be the volume distribution data of large platelets (such as the derived volume histogram of large platelets), the count value of large platelets or other characteristic parameters reflecting the volume distribution of large platelets.

In the fourth exemplary implementation, at step S270c, whether the test blood sample may contain schistocytes is determined based on the first volume distribution data acquired at step S250, the second volume distribution data acquired at step S255c and the red blood cell detection data acquired at step S257. If the determination result is yes, step S290 is executed to provide an alarm for indicating that the blood sample may contain schistocytes. If the determination result is no, the process ends. For specific contents on analyzing the first volume distribution data, the second volume distribution data and the red blood cell detection data, reference can be made to the contents of the second or the third exemplary implementation described above, which will not be repeated herein.

In the fourth exemplary implementation, alternatively, the step of outputting other detection results and/or intermediate results may further be included. The detection results include but not limited to the first volume distribution data acquired at step S250, the second volume distribution data acquired at step S255c and the red blood cell detection data acquired at step S257. The intermediate results include but not limited to the scattergram acquired at step S255c, the non-white blood cell region in the scattergram, the derived volume histogram, the curve portion of the larger particles separated by the derived volume separation threshold, and results acquired at each sub-step of step S270c.

Those skilled in the art should understand that all or part of the steps of the fourth exemplary implementation may be implemented by instructing related hardware of a blood analyzer through computer programs. The computer programs may be stored in a computer-readable storage medium and loaded into the blood analyzer having corresponding hardware system. When the computer programs are executed by a processor, the blood analyzer executes the analysis method for blood sample disclosed in the fourth exemplary implementation of the present disclosure.

The second aspect of the present disclosure further provides a blood analyzer. The blood analyzer includes a processor and a non-volatile computer-readable storage medium. The processor is configured to execute computer programs stored in the non-volatile computer readable storage medium to implement the steps of the analysis method of the fourth exemplary implementation.

The second aspect of the present disclosure further provides a non-volatile computer-readable storage medium storing computer programs thereon, wherein the computer programs, when executed by a processor, implement the steps of the analysis method of the fourth exemplary implementation. For the specific steps, reference can be made to various implementations and embodiments described above, which will not be repeated herein. Therefore, the analysis method of the fourth exemplary implementation may be implemented in the form of software function units and sold or used as an independent product.

Corresponding to the fourth exemplary implementation, the second aspect of the present disclosure further provides a blood analysis system. Please refer to FIG. 1 again, the blood analysis system includes a sample collection unit 10, a sample treatment device 30, a sample detection device 50, a data analysis module 70 and a user interface 90.

The sample treatment device 30 includes at least one mixing chamber, which is configured to mix a first aliquot of a blood sample with a diluent agent to obtain a first test sample, and mix a second aliquot of the blood sample with a lytic reagent to obtain a second test sample. The lytic reagent includes a hemolytic agent for lysing red blood cells.

The sample detection device 50 includes an electrical impedance detection unit 51 and an optical detection unit 53. The electrical impedance detection unit is configured to detect electrical impedance signals of the first test sample. The optical detection unit 53 is configured to detect at least two types of optical signals of the second test sample. The at least two types of optical signals include first scattered light signals and second scattered light signals, the first scattered light signals are forward scattered light signals, and the second scattered light signals are at least one of medium-angle scattered light signals and side scattered light signals.

The data analysis module 70 includes a signal acquisition module 750, a classification and counting module 770 and an alarm module 790. The signal acquisition module 750 acquires the electrical impedance signals of the first test sample and the at least two types of optical signals of the second test sample. The classification and counting module 770 acquires first volume distribution data of the blood sample based on the electrical impedance signals. The classification and counting module 770 generates a scattergram of the second test sample based on the at least two types of optical signals, differentiates a white blood cell region from a non-white blood cell region in the scattergram based on the at least two types of optical signals, and then acquires second volume distribution data of the blood sample based on the non-white blood cell region. The alarm module 790 acquires red blood cell detection data of the blood sample, determines whether the test blood sample may contain schistocytes based on the first volume distribution data, the second volume distribution data and the red blood cell detection data, and output an alarm for indicating that the blood sample may contain schistocytes if the determination result is yes. If the determination result is no, the process ends.

For specific implementations of other specific structures and function modules of the blood analysis system, reference can be made to corresponding contents described above, which will not be repeated herein.

Compared with the products and methods provided by the first aspect of the present disclosure, the blood analysis system, analysis method, blood analyzer and storage medium provided by the second aspect can provide an alarm for indicating schistocyte samples without using a fluorescence dye, and can provide users with more abundant detection information, and remind the users to perform a reexamination or recheck on the blood samples that may contain schistocytes without increasing the costs of the blood analysis system and the costs of the reagents used in the blood analysis process.

Figure 13:
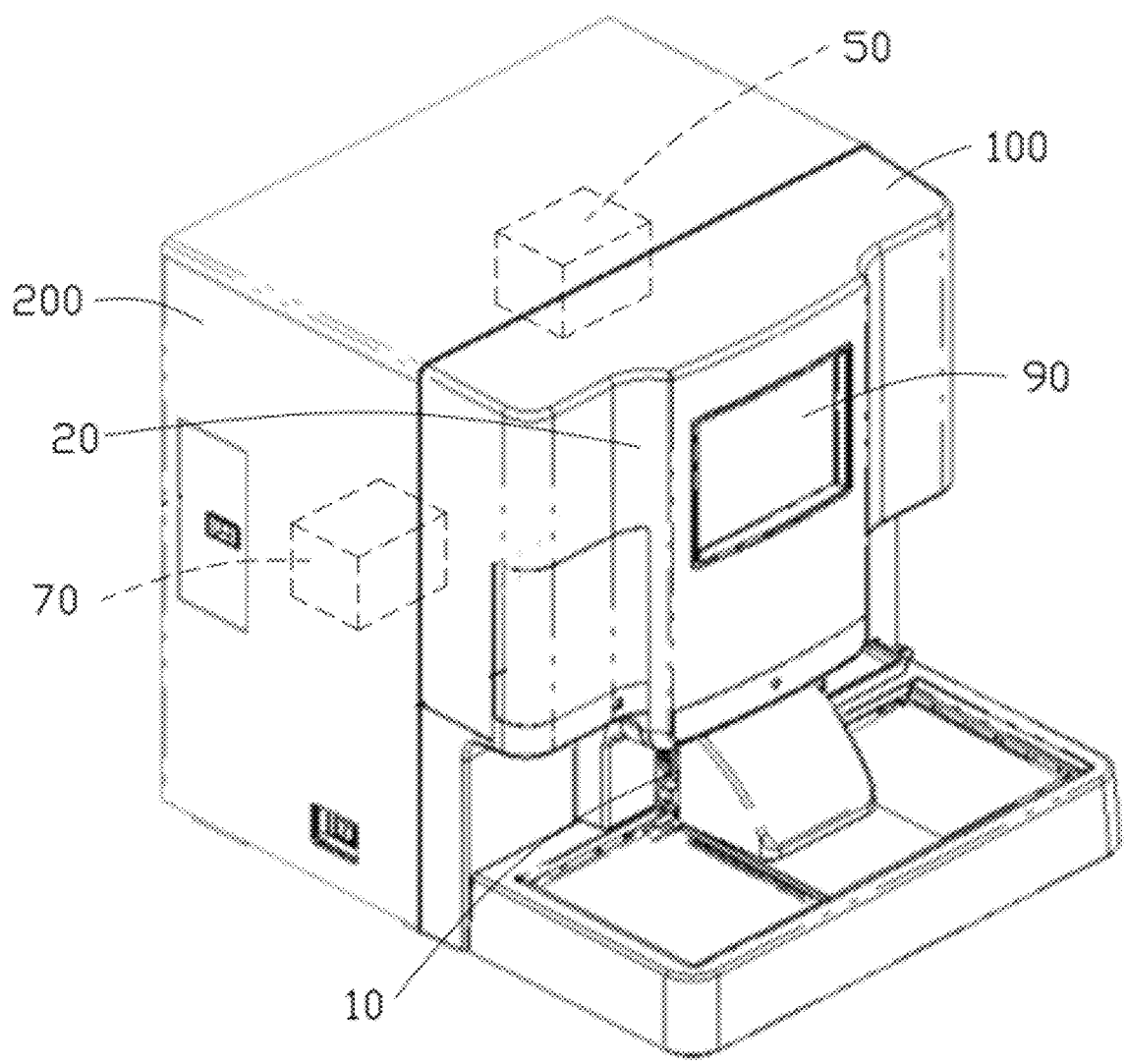
FIG. 13 is an overall stereoscopic diagram of a blood analysis system provided by the present disclosure.

FIG. 13 is an overall stereogram of a blood analysis system provided by the present disclosure. As shown in FIG. 13, the blood analysis system includes a first housing 100, a second housing 200, a sample collection unit 10, a sample treatment device 30, a sample detection device 50, a data analysis module 70 and a user interface 90. In the implementation, the sample detection device 50 and the data analysis module 70 are arranged inside the second housing 200, and are respectively arranged on both sides of the second housing 200. The sample treatment device 30 is arranged inside the first housing100. The user interface 90 and the sample collection unit 10 are arranged on the outer surface of the first housing100.

The above embodiments are preferable implementations of the present disclosure, but the present disclosure is not limited by the above embodiments, and the above implementations are only for interpreting claims. Any changes or replacements that can be easily conceived by those skilled in the art within the technical scope disclosed in the present disclosure are included within the protection scope of the present disclosure.

What is claimed is:

1. A blood analysis method, comprising the following steps:
   providing a blood sample;
   mixing a first aliquot of the blood sample with a diluent agent to prepare a first test sample;
   mixing a second aliquot of the blood sample with a lytic reagent to prepare a second test sample, wherein red blood cells in the second test sample are lysed by the lytic reagent;
   detecting electrical impedance signals of the first test sample;
   detecting at least two types of optical signals of the second test sample;
   acquiring first volume distribution data of the first test sample based on the electrical impedance signals;
   generating a scattergram of the second test sample based on the at least two types of optical signals; identifying a non-white blood cell region in the scattergram based on the at least two types of optical signals; and acquiring second volume distribution data of the second test sample based on the non-white blood cell region;
   acquiring red blood cell detection data of the blood sample;
   determining whether the blood sample may contain schistocytes based on the first volume distribution data, the second volume distribution data and the red blood cell detection data; and
   providing an alarm for indicating that the blood sample may be a sample containing schistocytes if the blood sample is determined to contain schistocytes.

2. The method according to claim 1, wherein the lytic reagent comprises a hemolytic agent for lysing red blood cells and a fluorescence dye for staining blood cells, and the at least two types of optical signals comprise forward scattered light signals and fluorescent signals; or
   wherein the lytic reagent comprises a hemolytic agent for lysing red blood cells, and the at least two types of optical signals comprise first scattered light signals and second scattered light signals, wherein the first scattered light signals are forward scattered light signals, and the second scattered light signals are at least one type of medium-angle scattered light signals and side scattered light signals.

3. The method according to claim 1, wherein acquiring second volume distribution data of the second test sample based on the non-white blood cell region comprises: acquiring the second volume distribution data of the second test sample based on at least forward scattered light signals of a particle population characterized in the non-white blood cell region, and acquiring a second particle number of particles within a preset volume range of the second volume distribution data; or
   wherein acquiring second volume distribution data of the second test sample based on the non-white blood cell region comprises: identifying a large platelet region in the non-white blood cell region; and acquiring a second particle number of the second test sample based on at least forward scattered light signals of a particle population characterized in the large platelet region; or
   wherein acquiring second volume distribution data of the second test sample based on the non-white blood cell region comprises: identifying a large platelet region in the non-white blood cell region; and acquiring a second particle number of the second test sample based on a number of particles in the large platelet region.

4. The method according to claim 3, wherein determining whether the blood sample may contain schistocytes comprises:
   acquiring a first particle number of particles within a preset volume range of the first volume distribution data; acquiring a difference degree by comparing the first particle number and the second particle number; and determining whether the difference degree meets a preset condition;
   determining whether the blood sample is a microcyte sample based on the red blood cell detection data; and
   determining that the blood sample may contain schistocytes when the difference degree meets the preset condition and the blood sample is not the microcyte sample.

5. The method according to claim 1, wherein determining whether the blood sample may contain schistocytes comprises:
   determining whether the first volume distribution data of the first test sample is abnormal;
   acquiring a second particle number based on the second volume distribution data of the second test sample, and determining whether the second particle number exceeds a threshold;

determining whether the blood sample is a microcyte sample based on the red blood cell detection data; and
determining that the blood sample may contain schistocytes when the first distribution data is abnormal, the second particle number does not exceed the threshold and the blood sample is not the microcyte sample.

6. The method according to claim 4, wherein acquiring red blood cell detection data of the blood sample comprises:
acquiring a mean corpuscular volume of the blood sample based on the electrical impedance signals;
wherein determining whether the blood sample is the microcyte sample based on the red blood cell detection data comprises:
determining whether the mean corpuscular volume is greater than a preset threshold of mean corpuscular volume; and
when the mean corpuscular volume is greater than the preset threshold of mean corpuscular volume, the blood sample is not the microcyte sample.

7. The method according to claim 4, wherein acquiring red blood cell detection data of the blood sample comprises:
acquiring volume distribution data of red blood cells of the blood sample based on the electrical impedance signals; and acquiring a volume at a preset volume percentage quantile of red blood cells based on the volume distribution data of red blood cells;
wherein determining whether the blood sample is the microcyte sample based on the red blood cell detection data comprises:
determining whether the volume at the preset volume percentage quantile of red blood cells is greater than a preset threshold; and
when the volume at the preset volume percentage quantile of red blood cells is greater than the preset threshold, the blood sample is not the microcyte sample.

8. The method according to claim 1, wherein the at least two types of optical signals comprise scattered light signals and fluorescent signals, and the method further comprises:
classifying white blood cells in the sample into white blood cell subpopulations, or counting white blood cells, or identifying nucleated red blood cells or immature cells or basophils, based on the scattered light signals and the fluorescent signals of the second test sample; or
classifying white blood cells in the sample into white blood cell subpopulations or identifying basophils based on scattered light signals of the second test sample.

9. A non-volatile computer-readable storage medium with a computer program stored thereon, wherein the computer program is programmed to implement the following steps:
detecting electrical impedance signals of a first test sample, wherein the first test sample is prepared by mixing a first aliquot of a blood sample with a diluent;
detecting at least two types of optical signals of a second test sample, wherein the second test sample is prepared by mixing a second aliquot of the blood sample with a lytic reagent, wherein red blood cells in the second test sample are lysed by the lytic reagent;
acquiring first volume distribution data of the first test sample based on the electrical impedance signals; generating a scattergram of the second test sample based on the at least two types of optical signals;
identifying a non-white blood cell region in the scattergram based on the at least two types of optical signals; and acquiring second volume distribution data of the second test sample based on the non-white blood cell region;
acquiring red blood cell detection data of the blood sample;
determining whether the blood sample may contain schistocytes based on the first volume distribution data, the second volume distribution data and the red blood cell detection data; and
providing an alarm for indicating that the blood sample may be a sample containing schistocytes if the blood sample is determined to contain schistocytes.

10. A blood analysis system, comprising:
a sample treatment device comprising at least one mixing chamber, which is configured to mix a first aliquot of a blood sample with a diluent agent to prepare a first test sample, and mix a second aliquot of the blood sample with a lytic reagent to prepare a second test sample;
a sample detection device comprising an electrical impedance detection unit and an optical detection unit, wherein the electrical impedance detection unit comprises an aperture and an electrical impedance detector, and the electrical impedance detector is configured to detect electrical impedance signals of the first test sample passing through the aperture; the optical detection unit comprises an optical flow chamber, a light source and an optical detector, wherein the optical flow chamber is in fluid communication with the mixing chamber, the light source is configured to direct a light beam to the optical flow chamber, and the optical detector is configured to detect at least two types of optical signals of the second test sample passing through the optical flow chamber;
a data analysis module comprising a signal acquisition module, a classification and counting module and an alarm module;
wherein the signal acquisition module is configured to acquire the electrical impedance signals of the first test sample, and acquire the at least two types of optical signals of the second test sample;
the classification and counting module is configured to acquire first volume distribution data of the first test sample based on the electrical impedance signals, generate a scattergram of the second test sample based on the at least two types of optical signals, differentiate a white blood cell region and a non-white blood cell region in the scattergram based on the at least two types of optical signals, and acquire second volume distribution data of the second test sample based on the non-white blood cell region; and
the alarm module is configured to acquire red blood cell detection data of the blood sample, determine whether the blood sample may contain schistocytes based on the first volume distribution data, the second volume distribution data and the red blood cell detection data, and provide an alarm for indicating that the blood sample may contain schistocytes if the blood sample is determined to contain schistocytes.

11. The blood analysis system according to claim 10, wherein the lytic reagent in the sample treatment device comprises a hemolytic agent for lysing red blood cells and a fluorescence dye for staining blood cells, and the at least two types of optical signals in the sample detection device comprise forward scattered light signals and fluorescent signals or comprise forward scattered light signals and side scattered light signals; or
wherein the lytic reagent in the sample treatment device comprises a hemolytic reagent for lysing red blood cells, and the at least two types of optical signals in the sample detection device comprise first scattered light signals and second scattered light signals, wherein the first scattered light signals are forward scattered light signals, and the second scattered light signals are at least one type of medium-angle scattered light signals and side scattered light signals.

12. The blood analysis system according to claim 10, wherein the classification and counting module is configured to acquire the second volume distribution data of the second test sample based on forward scattered light signals of a particle population characterized in the non-white blood cell region, and acquire a second particle number of particles within a preset volume range of the second volume distribution data; or wherein the classification and counting module is configured to identify a large platelet region in the non-white blood cell region, and acquire a second particle number of the second test sample based on at least forward scattered light signals of a particle population characterized in the large platelet region; or wherein the classification and counting module is configured to identify a large platelet region in the non-white blood cell region, and acquire a second particle number of the second test sample based on a number of particles appearing in the large platelet region.

13. The blood analysis system according to claim 12, wherein the alarm module is configured to acquire a first particle number of particles within a preset volume range of the first volume distribution data; acquire a difference degree by comparing the first particle number and the second particle number; and determine whether the difference degree meets a preset condition;

the alarm module is configured to determine whether the blood sample is a microcyte sample based on the red blood cell detection data; and the alarm module is configured to determine that the blood sample may contain schistocytes when the difference degree meets the preset condition and the blood sample is not the microcyte sample.

14. The blood analysis system according to claim 10, wherein the classification and counting module is configured to acquire a second particle number based on the second volume distribution data of the second test sample;

the alarm module is configured to acquire the first volume distribution data of the first test sample and determine whether the first volume distribution data is abnormal; and acquire the second particle number and determine whether the second particle number exceeds a threshold;

the alarm module is configured to determine whether the blood sample is a microcyte sample based on the red blood cell detection data; and determine that the blood sample may contain schistocytes when the first distribution data is abnormal, the second particle number does not exceed the threshold and the blood sample is not the microcyte sample.

15. The blood analysis system according to claim 13, wherein the red blood cell detection data comprise a mean corpuscular volume;

wherein the alarm module is configured to determine whether the mean corpuscular volume is greater than a preset threshold of mean corpuscular volume; when the mean corpuscular volume is greater than the preset threshold of mean corpuscular volume, the blood sample is not the microcyte sample.

16. The blood analysis system according to claim 13, wherein the red blood cell detection data comprise a volume at a preset volume percentage quantile of red blood cells;

wherein the alarm module is configured to determine whether the volume at the preset volume percentage quantile of red blood cells is greater than a preset threshold; when the volume at the preset volume percentage quantile of red blood cells is greater than the preset threshold, the blood sample is not the microcyte sample.

17. The blood analysis system according to claim 10, wherein the classification and counting module is further configured to classify white blood cells in the sample into white blood cell subpopulations, or count white blood cells, or identify nucleated red blood cells or immature cells or basophils based on scattered light signals and fluorescent signals of the second test sample; or wherein the classification and counting module is further configured to classify white blood cells in the sample into white blood cell subpopulations or identify basophils based on scattered light signals of the second test sample.

* * * * *